(12) United States Patent
Ogawa et al.

(10) Patent No.: US 9,930,887 B2
(45) Date of Patent: Apr. 3, 2018

(54) COMPOUND FOR INCREASING AMINO ACID CONTENT IN PLANT, AND USE THEREOF

(71) Applicant: Okayama Prefecture, Okayama (JP)

(72) Inventors: Kenichi Ogawa, Okayama (JP); Kenji Henmi, Okayama (JP); Aya Iwasaki, Okayama (JP)

(73) Assignee: OKAYAMA PREFECTURE, Okayama (JP)

( * ) Notice: Subject to any disclaimer, the term of this patent is extended or adjusted under 35 U.S.C. 154(b) by 148 days.

(21) Appl. No.: 14/364,477

(22) PCT Filed: Nov. 28, 2012

(86) PCT No.: PCT/JP2012/080771
§ 371 (c)(1),
(2) Date: Jun. 11, 2014

(87) PCT Pub. No.: WO2013/088956
PCT Pub. Date: Jun. 20, 2013

(65) Prior Publication Data
US 2014/0325712 A1    Oct. 30, 2014

(30) Foreign Application Priority Data
Dec. 12, 2011   (JP) .................. 2011-271662

(51) Int. Cl.
*A01N 37/02*    (2006.01)
*A01N 37/46*    (2006.01)
*A01N 41/12*    (2006.01)
*A01G 7/04*     (2006.01)

(52) U.S. Cl.
CPC ............. *A01N 37/46* (2013.01); *A01N 41/12* (2013.01); *A01G 7/045* (2013.01); *Y02P 60/146* (2015.11)

(58) Field of Classification Search
None
See application file for complete search history.

(56) References Cited

U.S. PATENT DOCUMENTS

| | | |
|---|---|---|
| 4,361,436 A | 11/1982 | McCarthy |
| 4,436,547 A | 3/1984 | Sampson |
| 5,211,738 A | 5/1993 | Sasaki |
| 5,256,558 A | 10/1993 | Coruzzi et al. |
| 5,350,689 A | 9/1994 | Shillito |
| 5,538,878 A | 7/1996 | Thomas |
| 5,595,733 A | 1/1997 | Carswell |
| 5,595,896 A | 1/1997 | Coruzzi et al. |
| 5,643,853 A | 7/1997 | Moore |
| 5,766,900 A | 6/1998 | Shillito |
| 5,770,450 A | 6/1998 | Shillito |
| 5,824,302 A | 10/1998 | Carswell |
| 5,869,456 A | 2/1999 | Levy |
| 5,872,216 A | 2/1999 | Hannah |
| 5,883,048 A | 3/1999 | Moore |
| 5,955,651 A | 9/1999 | Coruzzi et al. |
| 6,030,950 A | 2/2000 | Bernardis |
| 6,031,156 A | 2/2000 | Coruzzi et al. |
| 6,107,547 A | 8/2000 | Coruzzi et al. |
| 6,166,293 A | 12/2000 | Doerner |
| 6,442,486 B1 | 8/2002 | Satake |
| 6,559,358 B1 | 5/2003 | Murray |
| 6,751,576 B2 | 6/2004 | Hall et al. |
| 6,864,405 B1 | 3/2005 | Coruzzi |
| 7,479,267 B2* | 1/2009 | Ogawa .................... A01H 3/04 424/9.2 |
| 8,268,748 B2* | 9/2012 | Ogawa .................... A01N 37/46 504/116.1 |
| 8,575,428 B2* | 11/2013 | Kondo .................... A01N 37/46 800/290 |
| 8,927,286 B2* | 1/2015 | Ogawa .................... A01G 1/00 435/420 |
| 8,999,888 B2* | 4/2015 | Ogawa .................... A01N 37/46 504/100 |
| 2002/0069430 A1 | 6/2002 | Kisaka et al. |
| 2003/0110527 A1 | 6/2003 | Ogawa et al. |
| 2003/0115638 A1 | 6/2003 | Izui et al. |
| 2003/0177520 A1 | 9/2003 | Yanagisawa et al. |
| 2004/0052774 A1 | 3/2004 | Creissen |
| 2004/0133947 A1 | 7/2004 | Kisaka et al. |
| 2005/0114925 A1 | 5/2005 | Creissen |
| 2006/0123505 A1 | 6/2006 | Creissen |
| 2006/0183137 A1 | 8/2006 | Harper |
| 2007/0130643 A1 | 6/2007 | Kisaka et al. |
| 2008/0182752 A1 | 7/2008 | Izumori |
| 2008/0271200 A1 | 10/2008 | Dudits |
| 2009/0099023 A1 | 4/2009 | Ogawa et al. |
| 2010/0016166 A1 | 1/2010 | Ogawa et al. |
| 2010/0083404 A1 | 4/2010 | Ogawa et al. |
| 2010/0242141 A1 | 9/2010 | Ogawa |
| 2011/0078818 A1 | 3/2011 | Denes Dudits |
| 2011/0191898 A1 | 8/2011 | Crowley et al. |
| 2012/0324601 A1 | 12/2012 | Ogawa |
| 2014/0121100 A1* | 5/2014 | Habib ..................... C05G 3/02 504/100 |

FOREIGN PATENT DOCUMENTS

| | | |
|---|---|---|
| CA | 2652482 | 8/2007 |
| CN | 101583713 A | 11/2009 |

(Continued)

OTHER PUBLICATIONS

International Preliminary Report on Patentability dated Jun. 12, 2014, in corresponding PCT Application No. PCT/JP2012/080771.

(Continued)

*Primary Examiner* — Alton N Pryor
(74) *Attorney, Agent, or Firm* — Locke Lord LLP; James E. Armstrong, IV; Nicholas R. Herrel, Esq.

(57) ABSTRACT

In order to develop a technique for increasing an amino acid content and to provide a technique for easily producing a plant having an increased amino acid content, an amino acid content in a plant is increased by an amino acid content promoting agent, a composition containing the amino acid content promoting agent, a kit including an amino acid content promoting agent, or a kit including a composition containing the amino acid content promoting agent, and a plant having an increased amino acid content is produced.

9 Claims, 12 Drawing Sheets

(56) References Cited

FOREIGN PATENT DOCUMENTS

| | | |
|---|---|---|
| CN | 102076856 A | 5/2011 |
| EP | 0655196 A2 | 5/1995 |
| EP | 1992219 | 2/2007 |
| EP | 2208419 | 11/2008 |
| EP | 1277404 | 4/2011 |
| FR | 2710234 | 3/1995 |
| JP | 59-106407 | 6/1984 |
| JP | 62-100225 | 5/1987 |
| JP | 4-500369 | 1/1992 |
| JP | 4-217608 | 8/1992 |
| JP | 5-49470 | 3/1993 |
| JP | 6-199611 | 7/1994 |
| JP | 8-228621 | 9/1996 |
| JP | 9-503389 | 4/1997 |
| JP | 10-271924 | 10/1998 |
| JP | 10-323128 | 12/1998 |
| JP | 11-501034 A | 1/1999 |
| JP | 2000-38308 | 2/2000 |
| JP | 2000-300077 | 10/2000 |
| JP | 2000-515020 | 11/2000 |
| JP | 2001-505410 | 4/2001 |
| JP | 2001-288011 | 10/2001 |
| JP | 2001-519659 | 10/2001 |
| JP | 2001-346464 | 12/2001 |
| JP | 2004-264245 | 9/2004 |
| JP | 2004-267044 | 9/2004 |
| JP | 2004-352679 | 12/2004 |
| JP | 2005-052114 | 3/2005 |
| JP | 2005-110506 | 4/2005 |
| JP | 2005-130770 | 5/2005 |
| JP | 2006-141252 | 6/2006 |
| JP | 2006-188482 | 7/2006 |
| JP | 2007-131562 | 5/2007 |
| JP | 2007-530063 | 11/2007 |
| JP | 2008-070384 | 3/2008 |
| JP | 2009-165494 | 7/2009 |
| JP | 2010-166851 | 8/2010 |
| JP | 4621891 | 11/2010 |
| RU | 2126047 C1 | 2/1999 |
| RU | 2415573 C2 | 10/2011 |
| WO | WO 91/00008 | 1/1991 |
| WO | WO 00/5969 | 2/2000 |
| WO | WO 00/36911 | 6/2000 |
| WO | WO-01/80638 | 11/2001 |
| WO | WO 02/10210 | 2/2002 |
| WO | WO 02/33105 | 4/2002 |
| WO | WO-03/000041 | 1/2003 |
| WO | WO 2004/016726 | 2/2004 |
| WO | WO 2006/023782 | 3/2006 |
| WO | WO 2007/091634 | 8/2007 |
| WO | WO-2008/072502 | 5/2008 |
| WO | WO 2008/082602 | 7/2008 |
| WO | WO-2009/063806 | 5/2009 |

OTHER PUBLICATIONS

International Search Report dated Mar. 5, 2013, in corresponding PCT Application No. PCT/JP2012/080771.
Furudate et al., "Content and Composition of Free Amino Acids in Cabbage Grown under Various Cultivation Conditions", Journal of Home Economics of Japan (Nippon Kaseigaku Kaishi), vol. 53, No. 2, 199-203 (2002) (with partial English translation).
Hirota et al., "Effects of Soil and Fertilizer on Growth and Quality in Spinach (*Spinacia oleracea* L.)", Bull Hoygo Pre. Agri. Inst. (Agriculture) 50, 41-46 (2002) (with partial English translation).
Ma Lin "Absorption and Utilization of amino acids by plant", Journal of Southwest University of Science and Technology, vol. 19, No. 1, Mar. 2004, pp. 102-107.
Li Zhong "Informal discussion about amino acids of plants", Life World, 1990, No. 2, p. 36.
Wang Ying et al. "Absorption and Utilization of amino acids by plant and application of amino acids on agriclture", Soil and Fertilizer Science in China, 2008, No. 1, pp. 6-11.
Office Action dated Feb. 25, 2015, issued for the corresponding Chinese patent application No. 201280061106.1 and English translation thereof.
Noctor Graham et al., "Manipulation of Glutathione and Amino Acid Biosynthesis in the Chloroplast," Plant Physiol., 1998, 118, pp. 471-482.
2nd Office Action dated Aug. 28, 2105, issued for the Taiwanese patent application No. 101146054 and English translation thereof.
Final Office Action for U.S. Appl. No. 12/314,433, dated Jan. 10, 2017.
Sato T. Biosci. Biotechnol. Biochem., 66(12), 2543-2548, 2002.
Non-Final Office Action for U.S. Appl. No. 14/355,768, dated Jan. 12, 2017.
Final Rejection dated May 19, 2017 in connection with U.S. Appl. No. 14/355,768.
Restriction/Election Requirement for U.S. Appl. No. 14/355,768, dated Sep. 26, 2016.
Abbasi et al. Relationship Between Seed Colour and Linolenic Acid with Seed Yield and Yield Components of Flax (*Linum usitatissimum* L) in Isfahan. Journal of Water and Soil Science spring 2003, vol. 7, No. 1, abstract provided.
Non-Final Office Action for U.S. Appl. No. 12/314,433, dated Sep. 9, 2016.
Gautheret. The Nutrition of Plant Tissue Cultures. Annu. Rev. Plant. Physiol. (1955), 6: 433-484.
Non-Final Office Action for U.S. Appl. No. 14/473,001, dated Sep. 6, 2016.
Belmonte et al. The effects of reduced and oxidized glutathione on white spruce somatic embryogenesis. In Vitro Cell Dev. Biol. Plant 40:61-66. Jan.-Feb. 2004.
Allowance for Russian Patent Application No. 2014118883, dated May 30, 2016 (translation provided).
Pamin K. et al. Genetic variation and selection response for oil composition in corn// Crop Sc, T. 26, N 2, 1986, p. 279-282.
Brossman G.D., Wilcox J.R. Induction of genetic variation for oil properties and agronomic characteristics of soybean //Crop Sc, T. 24, N 4, 1984, p. 783-787.
Australian Office Action dated May 4, 2010. (Application No. 2007330795).
"Examiner's Report for Australian Application No. 2008321944 dated Sep. 13, 2010."
Office Action issued in related Australian Patent Application No. 2009224235 dated Dec. 16, 2011.
"Canadian Office Action dated Apr. 4, 2013, during prosecution of Canadian Patent Application No. 2,687,249."
China 2ndOA for 201280052993.6 dated Aug. 13, 2015 (with full English translation).
China 1st Office Action for 201280052993.6 dated Dec. 8, 2014 (with full English translation).
China Decision on Reexamination for 200780045685.X, dated Sep. 23, 2015 (with full English translation).
"Supplementary European Search Report for European Application No. 08849628.6, dated Dec. 22, 2011".
European Examination Report dated May 21, 2012 in European Application No. 10 180 526.5.
Extended European Search Report dated Nov. 18, 2010 in European Application No. 10180526.5.
European Examination Report dated May 23, 2012 in European Application No. 10 180 963.0.
European Examination Report dated Jun. 1, 2012 in European Application No. 09 009 268.5.
European Examination Report dated Apr. 6, 2011 in European Application No. 01 922 034.2.
European Examination Report dated Nov. 8, 2010 in European Application No. 01 922 034.2.
European Examination Report dated Jun. 30, 2010 in European Application No. 01 922 034.2.
European Examination Report dated Nov. 4, 2008 in European Application No. 01 922 034.2.
European Examination Report dated Jul. 27, 2007 in European Application No. 01 922 034.2.
European Examination Report dated Feb. 13, 2006 in European Application No. 01 922 034.2.

(56) References Cited

OTHER PUBLICATIONS

Supplementary European Search Report dated May 2, 2005 in European Application No. 01 922 034.2.
Partial European Search Report dated Dec. 21, 2004 in European Application No. 01 922 034.2.
Examination Report dated May 8, 2012 in European Application No. 10 002 403.3.
Examination Report dated Jul. 20, 2011 in European Application No. 10 002 403.3.
European Patent Office Search Report dated Nov. 17, 2010 in European Patent Application No. 10180963.
Extended European Search Report dated Oct. 19, 2010 in European Patent Application EP 10 00 2403.
Extended European Search Report dated Oct. 19, 2010 in European Patent Application No. EP 09 00 9268.
Partial European Search Report dated Jul. 19, 2010 in European Application No. 10002403.3.
Partial European Search Report dated Jul. 20, 2010 in European Application No. 09009268.5.
Office Action issued in the European Patent Application No. 01922034, dated Sep. 22, 2009.
Supplementary European Search Report for European Application No. EP-07850363, dated Dec. 1, 2011.
Office Action dated Sep. 19, 2012 from European Patent Application 07850363.8.
Office action dated Jul. 2, 2013, JP patent application No. 2011-545244 (with full English translation).
Japanese Office Action dated May 7, 2013, in Japanese Patent Application No. 2009-541115 (with full English translation).
Notice of Reasons for Refusal dated Feb. 15, 2011 in JP Application No. 2007-312518. (with partial English translation).
English translation of Notice of Reasons for Refusal dated Oct. 2, 2007 in corresponding JP Application No. 2001-577748.
Decision to Grant issued in Russian Application No. 2009123026 dated Sep. 15, 2009. (with full English translation).
Notice of Allowance dated Oct. 4, 2011, for Russian Patent Application No. 2009139630, and English Translation.
Russia 174037, Aug. 6, 1965, Decision to Grant of RU2009123026 and its transtaion is attached.
U.S. Office Action for U.S. Appl. No. 12/518,581, dated Jun. 9, 2011.
U.S. Office Action for U.S. Appl. No. 12/518,581, dated Jul. 15, 2014.
U.S. Office Action for U.S. Appl. No. 12/518,581, dated Mar. 24, 2014.
U.S. Office Action for U.S. Appl. No. 12/518,581, dated Dec. 6, 2011.
U.S. Office Action for U.S. Appl. No. 14/473,001, dated Mar. 24, 2016.
U.S. 2nd Office Action for U.S. Appl. No. 13/514,402, dated Mar. 31, 2014.
U.S. Final Office Action for U.S. Appl. No. 13/514,402, dated Jul. 24, 2104.
U.S. Advisory Action for U.S. Appl. No. 13/514,402, dated Sep. 4, 2014.
U.S. Notice of Allowance for U.S. Appl. No. 13/514,402, dated Sep. 23, 2014.
U.S. Corrected Notice of Allowance for U.S. Appl. No. 13/514,402, dated Oct. 7, 2014.
U.S. 1st Office Action for U.S. Appl. No. 13/514,402, dated Nov. 1, 2013.
U.S. Office Action for U.S. Appl. No. 14/600,984, dated Mar. 24, 2016.
U.S. 1st Office Action for U.S. Appl. No. 13/586,612, dated Sep. 24, 2012.
U.S. Final Office Action for U.S. Appl. No. 13/586,612, dated Apr. 4, 2013.
U.S. Notice of Allowance for U.S. Appl. No. 13/586,612, dated Jun. 3, 2013.
"Office Action dated Feb. 24, 2012, in connection with U.S. Appl. No. 12/599,710".
"Office Action dated Nov. 22, 2011, in connection with U.S. Appl. No. 12/599,710".
"Office Action dated Aug. 17, 2011, in connection with U.S. Appl. No. 12/599,710".
U.S. 2nd Office Action for U.S. Appl. No. 12/314,433—dated Feb. 26, 2015.
U.S. 1st Office Action for U.S. Appl. No. 12/314,433—dated Dec. 19, 2013.
U.S. Final Office Action for U.S. Appl. No. 12/314,433—dated Dec. 8, 2015.
Final Office Action for U.S. Appl. No. 12/314,433—dated Oct. 17, 2014.
U.S. Final Office Action for U.S. Appl. No. 12/314,433—dated Dec. 14, 2010.
U.S. Advisory Action for U.S. Appl. No. 12/314,433—dated May 20, 2011.
U.S. 1st Office Action for U.S. Appl. No. 12/314,433,—dated Aug. 3, 2010.
U.S. Notice of Allowance for U.S. Appl. No. 12/879,581—dated Jul. 8, 2013.
U.S. 1st Office Action for U.S. Appl. No. 12/879,581,—dated Oct. 17, 2012.
U.S. Final Office Action for U.S. Appl. No. 10/258,234, dated Apr. 25, 2008.
U.S. Final Office Action for U.S. Appl. No. 10/258,234, dated Jun. 21, 2007.
U.S. Restrictions Requirement for U.S. Appl. No. 10/258,234, dated Sep. 2, 2003.
U.S. Notice of Allowance for U.S. Appl. No. 10/258,234, dated Oct. 1, 2008.
U.S. Advisory Action for U.S. Appl. No. 10/258,234, dated Aug. 8, 2007.
U.S. 6th Office Action for U.S. Appl. No. 10/258,234, dated Oct. 11, 2007.
U.S. 5th Office Action for U.S. Appl. No. 10/258,234, dated Nov. 1, 2006.
U.S. 4th Office Action for U.S. Appl. No. 10/258,234, dated Feb. 9, 2006.
U.S. 3rd Office Action for U.S. Appl. No. 10/258,234, dated May 12, 2005.
U.S. 2nd Office Action for U.S. Appl. No. 10/258,234, dated Aug. 25, 2004.
U.S. 1st Office Action for U.S. Appl. No. 10/258,234, dated Dec. 31, 2003.
WO International preliminary report on patentability (Chapter I) of PCT/JP2012/078073, dated Feb. 5, 2013.
WO International Search Report of PCT/JP2012/078073 dated Feb. 5, 2013.
WO English translation of International Search Report dated Mar. 15, 2011, International Patent Application No. PCT/JP2010/072137.
WO International Preliminary Examination Report (English translation) dated Mar. 25, 2002 in International Application No. PCT/JP01/03491.
WO "International Search Report dated Jul. 17, 2001 in International (PCT) Application No. PCT/JP01/03491."
K.C.Kim,et al.,"Photoperiodic Floral Induction in Pharbitis Cotyledons Affected by Polyamines and Ethylene" J.Plant Biol., Vo.38, No. 3,pp. 227-234,1995.
Digital Farming Technology Cao Wei-xing et al., p. 357, Science Press, Aug. 2008, first edition, Aug. 31, 2008, (with full English translation).
Yang et al.,"Relationships of Canopy Reflectance Spectra with Wheat Yield and Yield Components," Chinese Journal of Agrometeorogy, vo;29(3),pp. 338-342, Aug. 20, 2008.
Jiao et al.,"Monitoring crop yield using NOAA/AVHRR-based vegetation indices" Transactions of the CSAE,vol. 21(4),pp. 104-108,2005, Jul. 30, 2005 (with full English translation).
Tri-Panji Et. Al., 'Fatty acid composition of juvenile palm leaf and its possible application for prediction of yield potential' Proceedings of BTIG Workshop on Oil Palm Improvement through Biotechnology, p. 122-126, Dec. 1998.

(56) References Cited

OTHER PUBLICATIONS

"Application of Near Infrared Spectroscopy in Detection of quality of RIce",Chinese Agrliculture Press,p. 65, 2008, Oct. 31, 2008 (with full English translation).
Norby et al. Effects of Atmospheric Co2 Enrichment on the Growth and Mineral Nutrition of Qurecus alba Seedings in Nutrient-Poor Sool.(Plant Physiol. (1986) 82, 83-89).
Auderset et al. Stimulation of Root Formation by Thiol Compounds (HorthScience 31(2):240-242. 1996).
Le Roux et al. Micropropagation and tissue culture of Eucalyptus (Tree Physiology 9, 435-477 1991).
Imin, N., et al., "Factors involved in root formation in Medicago truncatula," Journal of Experimental Botany (2007), vol. 58(3), Advance Access pub. Dec. 6, 2006, pp. 439-451.
Belmonte, M.F., et al., "Glutathione-induced growth of embryogenic tissue of white spruce correlates with change sin pyrimidine nucleotide metabolism," Plant Science (2005), vol. 168, pub. 12, Nov. 12, 2004, pp. 803-812.
Belmonte, M.F., et al., "Alterations of the glutathione redox state improve apical meristem structure and somatic embryo quality in white spruce (*Picea glauca*)," Journal of Experimental Botany, vol. 56, No. 419, pp. 2355-2365, Sep. 2005, Advance Access Publication Jul. 4, 2005.
Sotelo, M., et al., "Micropropagation of Eucalyptus maidenii elite trees," Agrociencia (2007) vol. XI No. 1, pp. 81-89.
Asada, T., "Tree Propagation Technology and Research Topics on Afforestation at Corporate Level," Forestry Research Institute, Oil Paper Company Limited (Research note, Regulation of Plant Growth & Development vol. 41, No. 1, pp. 83-89 (2006), The Japanese Society for Chemical Regulation of Plants) (with partial English translation).
Ma et al., Sudy on regeneration system for alfalfa in Xinjiang, Xinjiang Nongye Kexue, 2005, vol. 42 No. 1, pp. 19-23.-ABS.
Kuk et al., Mechanism of paraquat tolerance in cucumber leaves of various stages, Weed Science, 2006, vol. 54 No. 1,pp. 6-15.
Plant Cell Physiology 43(10) • 1096-1105(2002).
Annals of Botany, vol. 43: 305-318 (1979).
Crop Science, vol. 43: 2206-2211 (2003).
Plant Physiology, vol. 84:1126-1131(1987).
Plant Cell Physiology 46(8); 1175-1189(2005).
Science 286:1960-1962(1999).
L-Buthionine (S,R)-Sulfoximine Product Sheet, [online] 2011, [retrieved Nov. 30, 2011], retrieved from URL:<http://www.chemspider.com/Chemical-Structure.106767.html>, pp. 1-2.
Harvest Index Definition. [online]. Dictionary.com, 2010 [retrieved on Jun. 4, 2010]. Retrieved from the Internet: URL<http://dictionary.reference.com/browse/harvest+index> 1 page.
Henmi K. et al., Database WP1, Week 200505, Thomson Scientific, AN 2005-042852, XP002663511.
Fei-Yi, T. et al., "A Comparative Study of the Effects of Abscisic Acid and Methyl Jasmonate on Seedling Growth on Rice" Plant Growth Regulation, vol. 21, No. 1, pp. 37-42 (1997).
Razem F. et al., "The RNA-binding protein FCA is an abscisic Acid Receptor" Nature, vol. 439, No. 7074, pp. 290-294 (2006).
Henmi K. et al., "A Possible Role of Glutathione and Glutathione Disulfide in Tracheary Element Differentiation in the Cultured Mesophyll Cells of Zinnia Elegans" Plant Cell Physiol., vol. 42, No. 6, pp. 673-676(2001).
Ogawa K. et al., "Association of Glutathione with Flowering in *Arabidopsis Thaliana*" Plant Cell Physiol., vol. 42, No. 5, pp. 524-530 (2001).
Ogawa, K. et al. "Level of Glutathione is Regulated by ATP-Dependent Ligation of Glutamate and Cysteine through Photosynthesis in *Arabidopsis thaliana*:Mechanism of Strong Interacion of Light Intensity with Flowering", Plant and Cell Physiology, vol. 45, No. 1, pp. 1-8.
Biochemical Organic Compounds for Research and Diagnostic Reagents, 1989. Sigma Chemical Company. p. 657, product No. G4251.
Biochemical and Biophysical Research Communications, vol. 133, No. 3, pp. 988-993 (1985).
Plant & Cell Physiology, vol. 45, No. 2, pp. 129-137 (2004).
Herschnach et al (Plant Cell Physiol. 1998 39(4): 447-451).
"Simoni et al. ""The Discovery of Glutathione by F. Gowland Hopkins and the Beginning of Biochemistry at Cambridge University"" J. Biol. Chem, vol. 277, No. 24, 2002".
Hopkins, et al. ""On Glutathione. A Thermostable Oxidation-reduction Systems"" J. Biol. Chem. (1992) 54, p. 527-563.
Wingsle, et al. ""Differential redox regulation by glutathione of glutathione reductase and CuZn-superoxide Dismutase Gene Expression in *Pinus sylvestris* L. needles"" Planta (1996) 198: p. 151-157.
Ogawa, K. et al. ""Fructose-1,6-Bisphosphate Aldolase is a Target Protein of Glutathionylation in *Arabidopsis* Chloroplasts"", XP003016751, 13th International Congress on Photosynthesis, HTTP://abstracts.co.allenpress.com/pweb/pwc2004/document/?ID+39705 (2007).
"Ito, H. et al. ""The Sugar-Metabolic Enzymes Aldolase and Triose-Phosphate Isomerase are Targets of Glutathionylation in *Arabidopsis thaliana*; Detection using Biotinylated Glutathione"", Plant Cell Physiol. (2003) 44(7); p. 655-660 (2003)".
P. B. Applewhlte, et al., "A role for spermidine in the bolting and flowering of *Arabldopsis*", Physlologla Plantarum, vol. 108, pp. 314-320, 2000.
N. Wada, et al., "Flower Induction by Polyamines and Related Compounds in Seedlings of Morning Glory (*Pharbitis nil* cv. *Kidachi*)", Plant Cell Physiol., vol. 35, No. 3, pp. 469-472, 1994.
R. Macknight, et al., ""FCA, a Gene Controlling Lowering Time in *Arabidopsis*, Encodes a Protein Containing RNA-Binding Domains"", Cell, vol. 89, pp. 737-745, 1997.
O. Tanaka, et al.,"Effect of Ferricyanide, Ferrocyanide and KCN on Growth and Flowering in the Short-Day Plant Lemna paucicostata 6746",Plant and Cell Physiol. vol. 24, No. 4, pp. 705-711, 1983.
"Kazoe", farm Chemicals Handpook, 1995 edition, C214.
Peter J. Lea, ""Primary Nitrogen Metabolism"", Chapter 7 in Plant Biochemistry, Dey and Harbome., eds., 305-306, 1997.
"Reese et al., ""Effects of Buthionine Sulfoximine on Cd-Binding Peptide Levels in Suspension-Cultured Tobacco Cells Treated with Cd, Zn, or Cu"", Plant Physiology, 84: 574-577, 1987."
A. Groover et al., ""Programmed cell death of plant tracheary elements differentiating in vitro"", Protoplasma, vol. 196, No. 3-4, pp. 197-211, 1997.
H. Fukuda, "Tracheary element differentiation", Plant Cell, vol. 9, No. 7, pp. 1147-1156, 1997.
L. Liu et al., ""Localization of hydrogen peroxide production in *Zinnia elegans* L. Stems"", Phytochemistry, vol. 52, No. 4, pp. 545-554, 1999.
K. Ogawa et al,, "A mechanism for promoting the germination of Zinnia elegans seeds by hydrogen peroxide Plant and Cell Physiology, vol. 42, No. 3, pp. 286-291, 2001."
S. Gallais et al., "Pyridine nucleotides and redox charges during germination of non-dormant and dormant caryopses of *Avena sativa* L", Journal of Plant Physiology, vol. 153, No. 5-6, pp. 664-669, 1998.
C. Chien et al., "Mechanism of hydrogen peroxide in improving the germination of Cinnamomum camphora seed", Seed Science and Technology, vol. 22, No. 2, pp. 231-236, 1994.
M.E.B. Naredo et al., "Responses to seed dormancy-breaking treatments in rices species", Seed Science and Technology, vol. 26, No. 3, pp. 675-689, 1998.
O. Fontaine et al., "Dormancy breakage of Hordeum vulgare seeds: Effects of hydrogen peroxide and scarification on glutathione level and glutathione reductase activity", Plant Phyiology_and Biochemistry, vol. 32, No. 5, pp. 677-683, 1994.
J. Kurepa, et al., "Oxidative stress tolerance and longevity in *Arabidopsis*: The late-flowering mutant gigantea is tolerant to paraquat", Plant Journal, vol. 14, No. 6, pp. 759-764, 1998.
Z. Ye, et al., "The developmental transition to flowering represses ascorbate peroxidase activity and induces enzymatic lipid peroxidation in leaf tissue in *Arabidopsis thaliana*", Plant Science, vol. 158, No. 1-2, pp. 115-127, 2000.

(56) References Cited

OTHER PUBLICATIONS

Z. Ye, et al., "The developmental transition to flowering represses ascorbate peroxidase activity and induces enzymatic lipid peroxidation in leaf tissue in *Arabidopsis thaliana*", Plant Biology, vol. 1999, p. 75, 1999.
K.P. Reddy, et al., Catalase activity in rice shoot apex during panicle initiation, Plant and Cell Physiology, vol. 26, No. 7, pp. 1419-1424, 1985.
B. Earnshaw, et al., "Control of Wild Carrot Somatic Embryo Development by Antioxidants'—A Probable Mode of action of 2,4-Dichlorophenmacetic Acid", Plant Physiol., vol. 85, pp. 273-276, 1987.
B. Earnshaw, et al.,"The Effect of Glutathione on Development in Wild Carrot Suspension Cultures", Biochemical and Biophysical Research Communications, vol. 133, No. 3, pp. 988-993, 1985.
R. Sanchez-Fernandez, et al., "Cell proliferation and hair tip growth in the *Arabidopsis* root are under mechanistically different forms of redox control", Proc. Natl. Acad. Sci., vol. 94, pp. 2745-2750, 1997.
T. Potikha, et al., "The Involvement of Hydrogen Peroxide in the Differentiation of Secondary Walls in Cotton Fibers", Plant Physiology, vol. 119, pp. 849-858, 1999.
E. Tarenghi, et al., "Polyamines, floral induction and floral developments of strawberry (*Fragaria ananassa* Duch.)", Plant Growth Regulation, vol. 17, pp. 157-165, 1995.
"Yamada, Yasuyuki, et al., ""Nucleic Acid in Callus Formation and in Redifferentiation of Callus in Nicotiana Tabacum"", Soil Science and Plant Nutrition, vol. 14, No. 1, 1968, pp. 35-38."
Formation of Callus and Redifferentiation of Shoots from *Arabidopsis thaliana* Petal and Sepal Explants, Memoirs of Osaka Kyoiku University. Ser. 3. Natural Science and Applied Science, vol. 49, No. 2, 2001, pp. 277-283, Abstract, <hap ://sciencelinks.jp/j-east/article/200115/000020011501A0457740.php>.
Nishi, Toyoyuki, et al., ""Organ Redifferentiation and Plant Restoration in Rice Callus"", Nature, vol. 219, Aug. 1968, pp. 508-509, Abstract, <http://www.nature.com/nature/journal/v219/n5153/abs/219508a0.html>.
"Shimada, T., et al., ""In Vitro Culture of Wheat Tissues. I. Callus Formation, Organ Redifferentiation and Single Cell Culture"",Canadian Journal of Genetics and Cytology, vol. 11, No. 2, 1969, pp. 294-304, Abstract, <h t t p ://www.nrcresearchpress.com/doi/abs/10.1139/g69-037?journalCode=cgc>."
"Ogura, Hisakazu, ""The effects of a morphactin, chlorflurenol, on organ redifferentiation from tobacco calluses cultured in vitro"", Journal of Plant Research, vol. 88, No. 1, 1975, pp. 1-8, Abstract, <http://www.springerlink.com/content/735413224084k5x6/>."
Habaguchi, Kazuo, ""Alterations in polyphenol oxidase activity during organ redifferentiation in carrot calluses cultured in vitro"", Plant Cell Physiol., vol. 18, Issue 1, 1977, pp. 181-189, Abstract, <h t t p://pcp.oxfordj ournals.org/content/18/1/181.abstract>.
McGraw-Hill Dictionary of Scientific and Technical Terms, Second Edition, McGraw-Hill, Inc., 1978, pp. 1337.
"Lappartient, Anne G., et al., ""Glutathione-Mediated Regulation of ATP Sulfurylase Activity, SO42- Uptake, and Oxidative Stress Response in Intact Canola Roots"", Plant Physiol., vol. 114, 1997, pp. 177-183."
"Rauser, Wilfried E., et al., ""Cysteine, γ-Glutamylcysteine, and Glutathione Levels in Maize Seedlings"", Plant Physlol., vol. 97, 1991, pp. 128-138."
Gupta, Ashima S., et al., ""Response of Photosynthesis and Cellular Antioxidants to Ozone in Populus Leaves"", Plant Physiol., vol. 96, 1991, pp. 650-655.
Howden, Ross, et al., "Cadmium-Sensitive Mutants of *Arabidopsis thaliana*", Plant Physiol., vol. 99, 1992, pp. 100-107.
"Smith, Ivan K., ""Stimulation of Glutathione Synthesis in Photorespiring Plants by Catalase Inhibitors"", Plant Physiol., vol. 79, 1985, pp. 1044-1047."
"Nieto-Sotelo, Jorge, et al., ""Effect of Heat Shock on the Metabolism of Glutathione in Maize Roots"", Plant Physiol., vol. 82, 1986, pp. 1031-1035."

"Koprivova, Anna, et al., ""Regulation of Sulfate Assimilation by Nitrogen in *Arabidopsis*"", Plant Physiology, vol. 122, Mar. 2000, pp. 737-746."
"Shi, Zheng-Zheng, et al., ""Glutathione synthesis is essential for mouse development but not for growth in culture"", PNAS. vol. 97, No. 10, May 9, 2000, pp. 5101-5106."
"Patterson, John W., et al., ""Reactions of Alloxan and Dialuric Acid with the Sulfhydryl Group"", J. Biol. Chem., vol. 177, 1949, pp. 197-204."
Elhiti, Mohamed, et al., ""Modulation of embryo-forming capacity in culture through the expression of *Brassica* genes Involved in the regulation of the shoot apical merlstem"", Journal of Experimental Botany, vol. 61, No. 14, 2010, pp. 4069-4085.
Streb, P., et al., ""Significance of antioxidants and electron sinks for the cold-hardening-induced resistance of winter rye leaves to photooxidative stress"", Plant, Cell and Environment, vol. 22, 1999, pp. 1225-1237.
Yoshida, Kaoru T., et al., ""Control of Organogenesis and Embryogenesis in Rice Calll"", Breeding Science, vol. 44, 1994, pp. 355-360.
"U. Sethi et al., ""Control of Cell Proliferation and Differentiation by Regulating Polyamine Biosynthesis in Cultures of *Brassica* and its Correlation with Glyoxalase-I Activity,"" Plant Science, vol. 56, No. 2, pp. 167-175, 1988."
"Phillips, Gregory and G.B. Collins, ""Induction and development of somatic embryos from cell suspension cultures of soybean,""Plant Cell Tissue Organ Culture, vol. 1, No. 2, pp. 123-129, 1981."
"M. Yanagida et al., ""The Vernalization-Induced Bolting Involeves Glutathione Redox Regulation in Eustoma Grandiflorum,"" Plant and Cell Physiol. (2001), vol. 42, No. Supplement, p. 578."
"K. Ogawa et al., ""Involvement of Glutathione in Flowering in *Arabidopsis thaliana*,"" Plant Cell Physiol. (2001), vol. 42, No. Supplemental, p. 578."
"Phillips, G. C. and G. B. Collins, ""Induction and Development of Somatic Embryos from Cell Suspension Cultures of Soybean Glycine-Max,"" Plant Tissue and Organ Culture (1981), Obtained from Database Biosis [Online]."
"Nitsan, J., ""Effect of Glutathione and Alloxan on the Photoperiodic Response of Xanthium,"" Nature, vol. 187, pp. 81-82, Jul. 2, 1960."
"0. Fontaine et al., ""Effect of glutathione on dormancy breakage in barley seeds,"" Plant Growth Regulation, vol. 16, pp. 55-58, 1995."
"Tanemura, Yasuko, ""Polyamine Enhances the Regeneration of Reduced Glutathione by the Activation of NADP-dependent Dehydrogenases in yeast"", Biomedical Reasearch, vol. 25, No. 2, pp. 69-74 (2004)."
Mapson, L.W., "The Estimation of Oxidized Glutathione" Biochem Journal, vol. 55, No. 4, 1953, pp. 714-717.
Z. Naturforsch, "Effects of Polyamines on Glutathione Reductase Activity in Spinach", vol. 63(c), 2008, pp. 260-266.
Willekens et al. (EMBO journal; vol. 16, No. 16, pp. 4806-4816, (1997)).
Gossett et al. (Plant Phsiol. (1996), 112: pp. 803-809).
Alvarez et al. (Cell, (1998) 92: pp. 773-784).
Velikova et al. (Plant Science, (2000) 151; pp. 59-66).
Henmi et al. (cited in IDS, Plant Cell Physiol. (2005), 46(11), pp. 1757-1765).
Caliskan et al.(The Plant Journal, (1998),15(2), pp. 165-171).
Finch-Savage (New Phytologist, (2006), 171:pp. 501-523).
Penfield et al. (Current Biology, pp. 2366-2370, (2006)).
Mary Paz Gonzalez-Garcia et al., "Negative Regulation of Abscisic Acid Signaling by the Fagus sylvatica FsPP2C1 Plays a Role in Seed Dormancy Regulation and Promotion of Seed Germination", Plant Physiology, 2003, 133: 135-144.
David Reyes et al., "Overexpression of a Protein Phosphatase 2C from Beech Seeds in *Arabidopsis* Shows Phenotypes Related to Abscisic Acid Responses and Gibberellin Biosynthesis", Plant Physiology, 2006, 141: 1414-1424.
Angela Saez et al., "Gain-of-function and loss-of-function phenotypes of the protein phosphatase 2C HAB1 reveal its role as a negative regulator of abscisic acid signalling", The Plant Journal, 2004, 37: 354-369.

(56) References Cited

OTHER PUBLICATIONS

S. Sato et al., "Structural Analysis of *Arabidopsis thaliana* Chromosomes 3. I. Sequence Features of the "Regions of 4,504,864 by Covered by Sixty P1 and TAC Clones"", Accession No. BAA95773, dated Feb. 14, 2004, DNA Res, 7(2):131-135, ncbi.nlm.nih.gov/sviewer/viewerfcgi?tool=portal&sendto=on&log$-seqv . . . (dated Jan. 20, 2012).

Y. Totoki et al., "Large-Scale Analysis of RI KEN *Arabidopsis* Full-length (RAFL) cDNAs", Accession No. BAF00337, dated Jul. 27, 2006 (Unpublished), ncbi.nlm.nih.gov/sviewer/viewerfcgi?tool=portal&sendto=on&log$-seqv . . . (dated Jan. 20, 2012).

X. Lin et al., "*Arabidopsis thallana* chromosome III BAC F18C1 Genomic Sequence", Accession No. AAF26133, dated Oct. 30, 2002 (Unpublished), ncbl.nlm.nih.gov/sviewer/viewerfcgi?tool=portal&sendto=on&log$-seqv . . . (dated Jan. 20, 2012).

C.J. Kim et al., ""*Arabidopsis* ORF Clones"", Accession No. AAM10415, dated Apr. 13, 2002 (Unpublished), ncbi.nlm.nih.gov/sviewer/viewerfcgi?tool=portal&sendto=on&log$-seqv . . . (dated Jan. 20, 2012).

E. Koesema et al., "*Arabidopsis* cDNA Clones", Accession No. AAK91405, dated Aug. 20, 2001 (Unpublished), http://www.ncbi.nlm.nih.gov/sviewer/viewerfcgi?tool=portal&sendto=on&log$-seqv . . . (dated Jan. 20, 2012).

Meinhard and Grill, FEBS Letters(2001)508:443-446.

Umbarasaite et al., Methods in Mol. Bio.(2011) 779:149-161.

Schweighofer et al,Trends in Plant Sci.(2004)9:236-243.

Tyburski et al. Glutathione and glutathione disulfide effect adventitious root formation and growth in tomato seedling cuttings. Acta Physiol. Plant (2010) 32: 411-417. Published online :Nov. 24, 2009.

Notification of Reasons for Refusal dated Oct. 27, 2015, Issued for the Japanese patent application No. 2013-549197 and English translation thereof.

\* cited by examiner

FIG. 5

| Metabolite | nmol/gFW | | | | | | | |
|---|---|---|---|---|---|---|---|---|
| | Cont | | 1mM GSSG | | 2mM GSH | | 3mM NH4NO3 | |
| | L0 | L8 | L0 | L8 | L0 | L8 | L0 | L8 |
| Trp | 6.7 | 5.6 | 4.9 | 3.9 | 5.4 | 3.7 | 4.9 | 4.1 |
| Tyr | 14 | 16 | 5.5 | 8.4 | 5.1 | 8.0 | 4.9 | 7.9 |
| Hydroxyproline | 3.2 | 2.6 | 6.2 | 5.3 | 6.8 | 5.4 | 2.8 | 2.5 |
| Met | 6.4 | 7.6 | 6.5 | 10 | 7.2 | 8.8 | 4.4 | 9.5 |
| Homoserine | 1.2 | 2.0 | 11 | 9.3 | 8.7 | 9.8 | 1.6 | 5.2 |
| β-Ala | 21 | 34 | 20 | 46 | 21 | 47 | 18 | 29 |
| Phe | 32 | 34 | 22 | 27 | 19 | 26 | 22 | 25 |
| Ile | 20 | 25 | 24 | 30 | 28 | 32 | 12 | 17 |
| Leu | 26 | 31 | 30 | 17 | 31 | 17 | 12 | 20 |
| Lys | 38 | 34 | 47 | 47 | 49 | 56 | 32 | 24 |
| Val | 70 | 65 | 128 | 59 | 138 | 55 | 57 | 50 |
| His | 30 | 26 | 144 | 80 | 138 | 105 | 31 | 23 |
| Gly | 21 | 95 | 210 | 538 | 122 | 393 | 19 | 129 |
| Pro | 174 | 139 | 404 | 765 | 482 | 772 | 118 | 182 |
| Thr | 460 | 365 | 497 | 810 | 563 | 861 | 391 | 482 |
| GABA | 597 | 263 | 539 | 939 | 634 | 929 | 174 | 115 |
| Ala | 814 | 669 | 796 | 386 | 777 | 336 | 672 | 612 |
| Ser | 1,074 | 1,779 | 1,258 | 3,955 | 1,036 | 4,082 | 582 | 1,414 |
| Asp | 1,689 | 978 | 1,536 | 828 | 1,842 | 794 | 1,657 | 1,180 |
| Asn | 258 | 209 | 1,896 | 1,127 | 1,914 | 1,341 | 402 | 243 |
| Glu | 2,371 | 1,432 | 2,285 | 3,880 | 2,282 | 4,059 | 2,413 | 1,509 |
| Arg | 36 | 50 | 2,680 | 1,812 | 2,654 | 2,583 | 34 | 41 |
| Gln | 1,362 | 1,717 | 13,786 | 7,386 | 15,719 | 8,924 | 1,958 | 1,612 |
| Cys | N.D. | N.D. | N.D. | N.D. | N.D. | N.D. | N.D. | N.D. |

FIG. 12a

| Each Amino Acid Content at GSSG Treatment (nmol/gFW) | | | | | | | |
|---|---|---|---|---|---|---|---|
| GSSG (mM) | cont | 0.1 | 0.2 | 0.5 | 1 | 2 | 5 |
| Cysteine | N.D. | N.D. | N.D. | N.D. | N.D. | N.D. | N.D. |
| Methionine | N.D. | N.D. | N.D. | 0.9 | N.D. | 2.2 | 25 |
| GABA | 195 | 85 | 173 | 110 | 135 | 184 | 209 |
| Glutamic Acid | 1986 | 1620 | 2489 | 2489 | 3184 | 4643 | 6295 |
| β Alanine | 11 | 7.7 | 17 | 17 | 22 | 29 | 42 |
| Aspartic Acid | 552 | 328 | 685 | 608 | 838 | 1348 | 2183 |
| Alanine | 462 | 313 | 353 | 434 | 705 | 817 | 2344 |
| Lysine | 11 | 13 | 16 | 9.2 | 15 | 21 | 58 |
| Threonine | 159 | 99 | 162 | 145 | 137 | 256 | 921 |
| Hydroxyproline | 1.8 | 1.1 | 2.3 | 2.5 | 2.6 | 3.6 | 12 |
| Leucine | 30 | 18 | 28 | 21 | 22 | 56 | 306 |
| Serine | 666 | 513 | 745 | 839 | 1302 | 1589 | 8106 |
| Tryptophane | 5.6 | 6.2 | 7.2 | 4.3 | 4.2 | 15 | 78 |
| Valine | 88 | 53 | 92 | 81 | 81 | 220 | 1227 |
| Tyrosine | 9.3 | 7.9 | 9.1 | 8.3 | 9.4 | 18 | 166 |
| Phenylalanine | 58 | 48 | 56 | 57 | 63 | 246 | 1052 |
| Proline | 232 | 190 | 603 | 755 | 1123 | 1599 | 6254 |
| Isoleucine | 32 | 22 | 35 | 34 | 97 | 455 | 1547 |
| Glycine | 59 | 82 | 89 | 97 | 132 | 400 | 5483 |
| Asparagine | 78 | 43 | 69 | 182 | 1223 | 3501 | 12489 |
| Histidine | 7 | 5.9 | 8.2 | 5.7 | 9.7 | 213 | 2297 |
| Homoserine | 1.4 | 1.2 | 1.3 | 3 | 17 | 157 | 748 |
| Glutamine | 108 | 128 | 171 | 203 | 1279 | 11327 | 61634 |
| Arginine | 4.2 | 4 | 4.9 | 4.5 | 8.7 | 214 | 4495 |
| Total Free Amino Acid Contents | 4756.3 | 3589 | 5816 | 6110.4 | 10409.6 | 27313.8 | 117971 |

FIG. 12b

| Ratios of each Free Amino Acid at GSSG Treatment (Quantities in Control Area are 1) | | | | | | | |
|---|---|---|---|---|---|---|---|
| GSSG (mM) | cont | 0.1 | 0.2 | 0.5 | 1 | 2 | 5 |
| Cysteine | N.D. | N.D. | N.D. | N.D. | N.D. | N.D. | N.D. |
| Methionine | N.D. | N.D. | N.D. | N.D. | N.D. | N.D. | N.D. |
| GABA | 1.00 | 0.44 | 0.89 | 0.56 | 0.69 | 0.94 | 1.07 |
| Glutamic Acid | 1.00 | 0.82 | 1.25 | 1.25 | 1.60 | 2.34 | 3.17 |
| β Alanine | 1.00 | 0.70 | 1.55 | 1.55 | 2.00 | 2.64 | 3.82 |
| Aspartic Acid | 1.00 | 0.59 | 1.24 | 1.10 | 1.52 | 2.44 | 3.95 |
| Alanine | 1.00 | 0.68 | 0.76 | 0.94 | 1.53 | 1.77 | 5.07 |
| Lysine | 1.00 | 1.18 | 1.45 | 0.84 | 1.36 | 1.91 | 5.27 |
| Threonine | 1.00 | 0.62 | 1.02 | 0.91 | 0.86 | 1.61 | 5.79 |
| Hydroxyproline | 1.00 | 0.61 | 1.28 | 1.39 | 1.44 | 2.00 | 6.67 |
| Leucine | 1.00 | 0.60 | 0.93 | 0.70 | 0.73 | 1.87 | 10.20 |
| Serine | 1.00 | 0.77 | 1.12 | 1.26 | 1.95 | 2.39 | 12.17 |
| Tryptophane | 1.00 | 1.11 | 1.29 | 0.77 | 0.75 | 2.68 | 13.93 |
| Valine | 1.00 | 0.60 | 1.05 | 0.92 | 0.92 | 2.50 | 13.94 |
| Tyrosine | 1.00 | 0.85 | 0.98 | 0.89 | 1.01 | 1.94 | 17.85 |
| Phenylalanine | 1.00 | 0.83 | 0.97 | 0.98 | 1.09 | 4.24 | 18.14 |
| Proline | 1.00 | 0.82 | 2.60 | 3.25 | 4.84 | 6.89 | 26.96 |
| Isoleucine | 1.00 | 0.69 | 1.09 | 1.06 | 3.03 | 14.22 | 48.34 |
| Glycine | 1.00 | 1.39 | 1.51 | 1.64 | 2.24 | 6.78 | 92.93 |
| Asparagine | 1.00 | 0.55 | 0.88 | 2.33 | 15.68 | 44.88 | 160.12 |
| Histidine | 1.00 | 0.84 | 1.17 | 0.81 | 1.39 | 30.43 | 328.14 |
| Homoserine | 1.00 | 0.86 | 0.93 | 2.14 | 12.14 | 112.14 | 534.29 |
| Glutamine | 1.00 | 1.19 | 1.58 | 1.88 | 11.84 | 104.88 | 570.69 |
| Arginine | 1.00 | 0.95 | 1.17 | 1.07 | 2.07 | 50.95 | 1070.24 |
| Total Free Amino Acid Contents | 1.00 | 0.75 | 1.22 | 1.28 | 2.19 | 5.74 | 24.80 |

FIG. 13

| | | GSSG Granules | | | GSH Granules | | |
|---|---|---|---|---|---|---|---|
| Days After Granule Treatment | | After 20 Days | After 29 Days | After 57 Days | After 20 Days | After 29 Days | After 57 Days |
| Ratios of each Free Amino Acid when Quantities in Control Area are 1. | Trp | 1.0 | 1.7 | 1.0 | 1.5 | 1.5 | 1.2 |
| | Cys | 1.2 | 2.4 | 1.3 | 2.1 | 1.7 | 1.3 |
| | Met | 1.0 | 2.0 | 1.0 | 1.1 | 1.6 | 1.2 |
| | Tyr | 1.0 | 3.8 | 1.1 | 2.3 | 2.4 | 1.1 |
| | Val | 1.3 | 3.6 | 1.0 | 2.3 | 2.4 | 1.1 |
| | Gly | 1.2 | 3.8 | 0.8 | 3.0 | 2.6 | 0.9 |
| | Ile | 1.3 | 3.7 | 1.0 | 1.9 | 2.3 | 1.0 |
| | Leu | 1.2 | 2.9 | 1.0 | 2.0 | 2.2 | 1.1 |
| | Arg | 1.3 | 2.3 | 1.0 | 1.2 | 1.7 | 1.1 |
| | Thr | 1.4 | 3.0 | 1.0 | 1.3 | 1.8 | 1.0 |
| | His | 1.2 | 2.8 | 1.3 | 1.3 | 2.0 | 1.4 |
| | Lys | 1.4 | 2.5 | 1.2 | 1.4 | 1.7 | 1.1 |
| | Phe | 1.2 | 1.9 | 1.3 | 1.5 | 1.9 | 1.5 |
| | Pro | 2.5 | 2.6 | 1.4 | 1.7 | 1.7 | 0.7 |
| | Ser | 1.4 | 3.2 | 1.0 | 1.2 | 1.9 | 1.1 |
| | Asn | 1.8 | 2.8 | 1.0 | 1.0 | 1.5 | 0.9 |
| | Ala | 1.2 | 4.5 | 0.9 | 2.3 | 2.2 | 1.1 |
| | Asp | 1.3 | 2.2 | 1.0 | 0.8 | 1.4 | 1.0 |
| | Gln | 1.7 | 2.2 | 1.1 | 0.8 | 1.4 | 0.9 |
| | Glu | 1.3 | 1.8 | 1.3 | 1.0 | 1.4 | 1.2 |
| Total Free Amino Acid Contents | | 1.4 | 2.2 | 1.1 | 1.1 | 1.5 | 1.1 |

COMPOUND FOR INCREASING AMINO ACID CONTENT IN PLANT, AND USE THEREOF

TECHNICAL FIELD

The present invention relates to a compound for increasing an amino acid content in a plant, a composition containing the compound, and use thereof.

BACKGROUND ART

Amino acids deeply relate to tastes of foods such as body, sweetness, etc. thereof, and, in addition, a biological activity of amino acids has attracted attention in recent years, especially. Accordingly, various products characterized by amino acid contents have been developed. Further, agricultural products are strongly interested in nutritional values thereof.

It is known that an amino acid content in a plant changes depending on a cultivation condition of the plant. For example, Non-patent Literature 1 discloses that a content and a composition of a free amino acid in cabbage change depending on a harvesting stage and a nitrogen fertilizing condition. Non-patent Literature 2 discloses that a free amino acid content in spinach differs depending on differences in soil and fertilizer.

It is also known a technique for producing vegetables having high amino acid contents. For example, Patent Literature 1 discloses a method of producing a vegetable having a high amino acid content, in which method a nitrogen fertilizer is supplied to the vegetable at a harvesting stage thereof. Patent Literatures 2 through 4 each disclose that a free amino acid content is increased in a plant transformed with a certain gene.

CITATION LIST

Patent Literature

Patent Literature 1
Japanese Patent Application Publication, Tokukaihei, No. 10-323128 A (Publication date: Dec. 8, 1998)
Patent Literature 2
Japanese Patent Application Publication, Tokukai, No. 2003-125661 A (Publication date: May 7, 2003)
Patent Literature 3
Japanese Patent Application Publication, Tokukai, No. 2003-310072 A (Publication date: Nov. 5, 2003)
Patent Literature 4
Pamphlet of International Publication WO 2003/000041 (Publication date: Jan. 3, 2003)
Patent Literature 5
Japanese Patent Application Publication, Tokukai, No. 2004-352679 A (Publication date: Dec. 16, 2004)
Patent Literature 6
Japanese Patent Application Publication, Tokukai, No. 2009-165494 A (Publication date: Jul. 30, 2009)
Patent Literature 7
Japanese Patent Application Publication, Tokukai, No. 2008-120815 A (Publication date: May 29, 2008)
Patent Literature 8
Pamphlet of International Publication WO 01/080638 (International Publication date: Nov. 1, 2001)
Patent Literature 9
Pamphlet of International Publication WO 2008/072602 (International Publication date: Jun. 19, 2008)
Patent Literature 10
Pamphlet of International Publication WO 2009/063806 (International Publication date: May 22, 2009)

Non-Patent Literatures

Non-Patent Literature 1
Bull. Hyogo Pre. Agri. Inst. (Agriculture) 50, 41-46 (2002)
Non-Patent Literature 2
Journal of Home Economics of Japan (*Nippon Kaseigaku Kaishi*), Vol. 53, No. 2, pp. 199-203 (2002)

SUMMARY OF INVENTION

Technical Problem

However, in order to obtain a plant whose amino acid content is increased by twice or more times, it is necessary to use genetic recombination techniques disclosed in Patent Literatures 2 through 4, and an effect of increasing an amino acid content merely by using growing management as disclosed in Patent Literature 1 is small.

The present invention has been made in view of the above problems, and an object of the present invention is to develop a technique for increasing an amino acid content in a plant and to provide a technique for easily producing a plant having an increased amino acid content.

Solution to Problem

The inventors of the present invention have diligently studied to attain the object. Accordingly, the inventors succeeded in remarkably increasing an amino acid content in a plant by growing the plant to which glutathione had been administrated under a certain condition(s). This effect has such a high level that using conventional nitrogen fertilizers as disclosed in Patent Literature 1 cannot achieve. As disclosed in Patent Literatures 2 through 4, plants having remarkably increased amino acid contents have been produced by using genetic recombination techniques, however, it has never been reported that an amino acid content in a plant is remarkably increased merely by growing management.

The inventors of the present invention found that a callus could be regenerated efficiently with use of glutathione in a short term (Patent Literatures 5, 6, etc.), regeneration of cells or organs could be regulated (Patent Literatures 7, 8, etc.), a harvest index of a plant could be increased (Patent Literature 9 etc.), and a sugar content in a plant could be increased (Patent Literature 10 etc.). However, it has never been reported that an amino acid content in a plant is increased by supplying glutathione. Further, capable of increasing an amino acid content in a plant with ease is a remarkable effect that is beyond expectation for a person skilled in the art.

A composition of the present invention contains an amino acid content promoting agent to increase an amino acid content in a plant.

A kit of the present invention contains the amino acid content promoting agent or includes a composition containing the amino acid content promoting agent to increase an amino acid content in a plant.

The composition and the kit of the present invention may be used to produce a plant having an increased amino acid content.

A method of the present invention includes the step of supplying an amino acid content promoting agent or a composition containing the amino acid content promoting agent to a plant.

A producing method of the present invention includes the step of cultivating a plant in the presence of an amino acid content promoting agent.

A plant of the present invention is produced by the above producing method.

Advantageous Effects of Invention

The present invention does not need to use genetic recombination techniques, and, in addition, is applicable to any kind of plant. Therefore, the present invention can be applied to various crops and fruit trees. The present invention can strengthen a brand power of a desired agricultural product and contribute creation of a new brand of an agricultural product by increasing an amino acid content in the agricultural product.

By using the present invention, it is possible to advance and/or increase a content and a composition of an amino acid of an agricultural product. This makes it possible to apply a large added value to agricultural products. For example, by using the present invention, it is expected to increase amino acid contents of agricultural products such as garland chrysanthemum (*Chrysanthemum coronarium*), spinach (*Spinacia oleracea*), Japanese mustard spinach (*Brassica campestris* var. *perviridis*), Butterhead lettuce (L.s. var *capitata*), Choy sum (*Brassica rapa* var. *utilis*), cabbage (*Brassica oleracea* var. *capitata*), carrot (*Daucus carota*), tea plant (*Thea sinensis*), green soybeans (*Glycine max*), etc., and it is possible to contribute to development of vegetables approved as Food For Specified Health Uses having high functionalities and high added values. In addition, a plant grown with use of the present invention can be easily specified by analyzing metabolites of agricultural products or by carrying out analysis with use of isotopes of carbon, nitrogen, and/or sulfur. Therefore, the right of the present invention can be easily executed.

BRIEF DESCRIPTION OF DRAWINGS

FIG. 5 is a view showing each amino acid content in each leaf of *Arabidopsis* to which glutathione has been supplied and which has been regulated in terms of a light condition before harvesting.

FIG. 12a is a view showing each free amino acid content in garland chrysanthemum to which glutathione having various concentrations has been supplied.

FIG. 12b is a view showing each free amino acid content in garland chrysanthemum to which glutathione having various concentrations has been supplied assuming that such a quantity under a control condition (cont.) is 1.

FIG. 13 is a view showing each free amino acid content in a fruit of tomato to which granular glutathione has been supplied.

DESCRIPTION OF EMBODIMENTS

Figure 1:
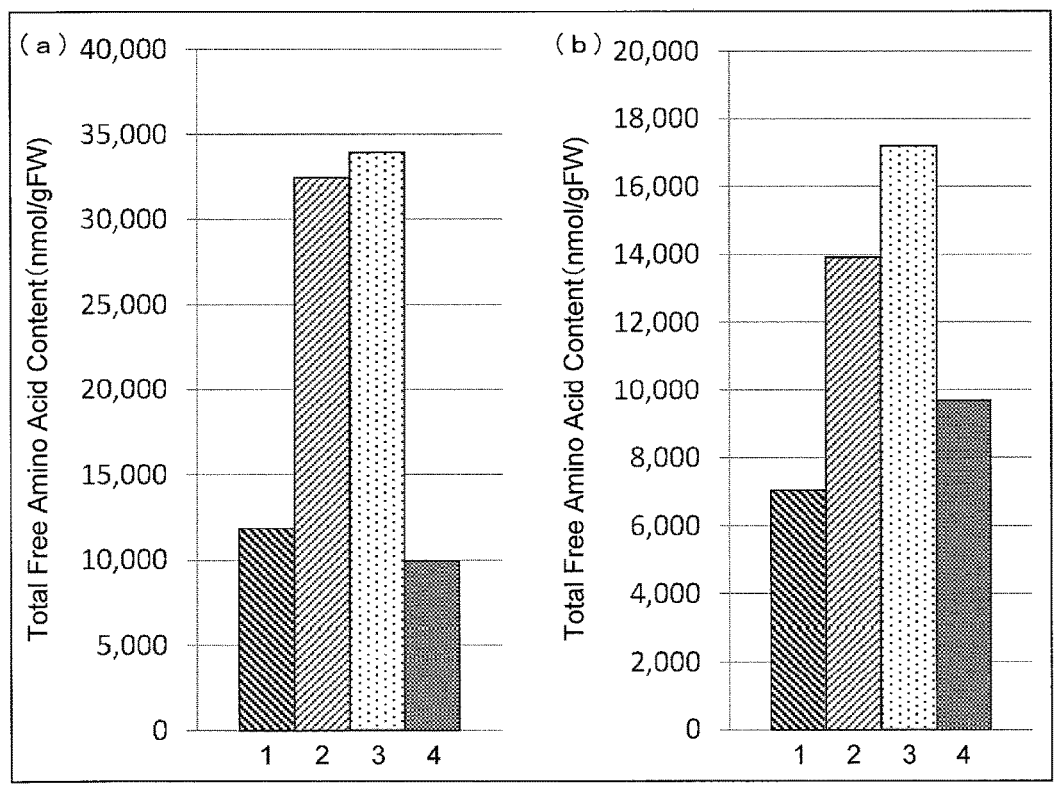
FIG. 1 is graphs showing total free amino acid contents contained in thale cress (*Arabidopsis*) (*Arabidopsis thaliana*) which has been grown under various cultivation conditions after 4 weeks from seeding (a) and after 5 weeks from the seeding (b).

The following description will discuss one embodiment of the present invention. Note that the present invention is not limited thereto.

[1. Amino Acid Content Promoting Agent]

The wording "amino acid content promoting agent" in the specification of the subject application means a substance that can increase an amino acid content in a plant, and a substance increasing synthesis of glutathione and a glutathione production amount is also included in the amino acid content promoting agent. In the present invention, the amino acid content promoting agent is preferably taken up into a plant by being contacted with the plant, thereby acting on the plant, and more preferably, the amino acid content promoting agent is glutathione or a derivative thereof.

As shown in Examples described below, all amino acid contents were remarkably increased in a plant which had been cultivated with use of oxidized glutathione or reduced glutathione, as compared with a plant cultivated under a regular condition or a plant cultivated with use of ammonium nitrate. Further, contents of certain amino acids (e.g., alanine, serine, proline, valine, tyrosine, isoleucine, leucine, asparagine, aspartic acid, glutamine, glutamic acid, methionine, histidine, arginine, GABA, hydroxyproline, and homoserine) were increased to a specially remarkable degree that is beyond expectation for a person skilled in the art on the basis of conventional arts which increase an amino acid content in a plant merely with use of growing management.

Glutathione having a detoxifying effect and an antioxidation effect in vivo is tripeptide consisting of γ-Glu-Cys-Gly and is a storage form and a transportation form of sulfur in a plant. Example derivatives of glutathione encompass homoglutathione, carboxypropyl glutathione, and dicarboxyethyl glutathione, however, the example derivatives are not limited thereto provided that the derivatives have a function of increasing an amino acid content in a plant as glutathione does. Homoglutathione in a leguminous plant, which has a similar function to that of glutathione, is a compound in which Gly of glutathione is replaced with β-Ala. Further, esters of glutathione or the derivatives are also encompassed in derivatives of glutathione. That is, an amino acid content promoting agent for use in the present invention can be a substance selected from the group consisting of oxidized glutathione, reduced glutathione, homoglutathione, carboxypropyl glutathione, dicarboxyethyl glutathione, and ester thereof.

Glutathione for use in the present invention are not particularly limited in terms of producing conditions thereof, and may be artificially synthesized or derived from natural products. In addition, a degree of refinement may be high and low, and commercially available glutathione may be used.

Glutathione or derivatives thereof may be reduced or oxidized, however, in many cases, glutathione or derivatives thereof are preferably oxidized.

The inventors of the present invention have researched a mechanism of germinating, growing, and blooming of plants so far, and found the following things: culturing a callus derived from a part of a plant body in a regeneration medium containing glutathione promotes rooting, thereby efficiently obtaining a regeneration body from the callus in a short term (Patent Literature 5 etc.); the number of seeds and the number of flowers of the cultivated plant can be remarkably increased by cultivating a plant with use of glutathione, and, by cultivating, with use of glutathione, a plant body having a varied synthesis function and a varied response function of phytohormone (e.g., gibberelline), lateral buds can be remarkably increased, and accordingly the number of flowers (pods) can be also increased (Patent Literature 8 etc.); and a sugar content in a plant body is increased (Patent Literature 10 etc.). However, the use of glutathione or derivatives thereof as an amino acid content promoting agent is a novel use. In other words, the use of glutathione or derivatives thereof to easily increase an amino acid content in a plant is a novel use. That is, the above use of glutathione or derivatives thereof is completely different use from conventional use thereof. Further, obtaining plants having increased amino acid contents is beyond expectation from the conventional use. As described above, the present invention has been made by the inventors of the present invention on the basis of completely novel findings.

In order to achieve such a use, an amino acid content promoting agent may be directly used as a compound, may be used in the form of a composition containing the amino acid content promoting agent, or may be used in the form of the amino acid content promoting agent or the composition provided in a kit. Generally, the composition means that "two or more kinds of components exist uniformly as a whole and those components are regarded as a single substance", and, in a case where the composition is used in the present specification, the "composition" means a form in which various kinds of components are contained in a single substance. The "kit" for use in the present specification means a form in which various kinds of components to be contained in the composition are included in separate containers (e.g., bottle, plate, tube, dish, etc.) and all the containers are packed into one as a whole, and may include a support or a culturing container described later.

By using the amino acid content promoting agent, an amino acid content in a plant can be easily increased, and a plant having an increased amino acid content can be also produced. For example, a plant may be cultivated with use of a medium in which the amino acid content promoting agent is contained, or the amino acid content promoting agent may be scattered over, dropped toward, or applied in a liquid composition to a whole plant body or a part (stem, leaf, or the like) of a plant body. Further, in a case where a plant is an aquatic plant such as a water grass, the amino acid content promoting agent may be taken up from a root thereof as a bottom additive or may be dissolved in a solid composition in water gradually. Therefore, in comparison with the conventional arts described above, it is possible to easily increase an amino acid content in a plant without proficient skills, special techniques, special production devices, etc. and to easily obtain a plant having an increased amino acid content.

The wording "plant having an increased amino acid content" for use in the present specification means a plant whose amino acid content is increased in comparison with a same kind of plant which is cultivated in the absence of the amino acid content promoting agent. In a case where the amino acid content promoting agent is used to cultivate a plant, the amino acid content in the plant can be increased in comparison with a case where the amino acid content promoting agent is not used to cultivate the plant. Note that a method of measuring an amino acid content in a plant may be carried out in accordance with conventional known procedures.

In a case where oxidized glutathione (GSSG) is supplied to a plant as a liquid composition, a use concentration of the amino acid content promoting agent is preferably 0.2 mM to 5 mM, more preferably 0.5 mM to 5 mM, further preferably 1 mM to 5 mM, and further more preferably 2 mM to 5 mM. Within the above range, it is possible to more increase an amino acid content in a plant to be produced. The liquid composition can be prepared by dissolving the amino acid content promoting agent in an appropriate solvent (e.g., water or the like). As water, any of deionized water, distilled water, reverse osmosis water, tap water, etc. can be used. Components other than the amino acid content promoting agent, such as various kinds of fertilizers, detergents (surface-active agents), etc. which are commercially available, can be contained in the solvent. Note that the use concentration can be changed appropriately in accordance with the kind of plants to be applied and an application season.

An amount of the amino acid content promoting agent to be applied to a plant can be regulated in accordance with the concentration and supply conditions thereof, and the amount can be determined on the basis of a total amount of the amino acid content promoting agent to be actually applied to a plant.

For example, as a method of wetting a support with the amino acid content promoting agent for use in cultivation of a plant, there are, for example, a method in which a solution containing the amino acid content promoting agent is scattered over the support from the above, a method in which the support is placed in a container filled with a solution containing the amino acid content promoting agent and caused to be wetted from a bottom of the support. In a case of scattering the solution over the support from the above, an amount of the solution scattered from the above can be appropriately adjusted in accordance with cultivation conditions such as a use condition of the amino acid content promoting agent, a volume of a pot, etc. For example, assuming that 1 mM of GSSG is used, it is preferable to use 5 mL/time to 150 mL/time per individual, more preferably 8.5 mL/time to 100 mL/time, and further preferably 20 mL/time to 50 mL/time. In a case of wetting the solution from the bottom, the support only needs to be wet by the solution containing the amino acid content promoting agent substantially uniformly. As the amount and concentration of the solution for use in such a case, it is also possible to determine an amount of the amino acid content promoting agent to be supplied per soil.

In a case of directly scattering the liquid composition over a plant, the solution may be sprayed toward a part of or a whole plant with use of a spray or the like. An amount of the solution are appropriately determined in accordance with the concentration of the amino acid content promoting agent in the solution. The number of times of scattering the solution may be one or two or more, and it is preferable to scatter the solution when cultivation of a plant is started. Further, the solution may be additionally scattered as appropriate in accordance with a use condition of the amino acid content promoting agent (e.g., every other several days (2 days to 7 days)) during a cultivation period.

Note that a medium or a solution containing the amino acid content promoting agent is preferably provide to a plant after the amino acid content promoting agent is adjusted within the above concentration, however, the amino acid content promoting agent only needs to have been mixed with a medium or a solution before/when the amino acid content promoting agent is taken up into a plant. Therefore, a medium or solution not containing the amino acid content promoting agent and an adjuvant may be directly provided simultaneously or successively to an outer surface of a plant, or may be provided to a periphery (support or soil) of the plant. By employing such a process, a plant can take up a medium or solution with which the adjuvant is mixed.

[2. Composition for Increasing Amino Acid Content in Plant]

The present invention provides a composition for increasing an amino acid content in an plant (hereinafter, referred to also as "composition of the present invention"). The composition of the present invention is only necessary to contain the amino acid content promoting agent.

By using the composition of the present invention in the same way as the above amino acid content promoting agent, it is possible to easily increase an amino acid content in a plant, and further to produce a plant having an increased amino acid content.

As described above, the amino acid content promoting agent of the present invention is preferably glutathione or derivatives thereof. Glutathione have reduced glutathione (hereinafter, referred to as "GSH") and oxidized glutathione (hereinafter, referred to as "GSSG"), and any glutathione may be employed for the present invention. Regardless of whether GSSG is used or GSH is used, it is possible to obtain a plant having all amino acid contents higher than those of a plant under a control condition as described in Examples below. Note that the "oxidized glutathione" is defined as a molecule in which two molecules of reduced glutathione are attached to each other via a disulfide bond. Note that it is well known for a person skilled in the art that GSH is apt to be oxidized. Therefore, GSH is caused to be contained in a composition of the present invention as the amino acid content promoting agent, the composition of the present invention contains GSSG to some extent. In other words, the composition of the present invention may contain both GSH and GSSG as glutathione. The composition of the present invention may be used in such a manner that the composition contains GSH and the GSH is oxidized to become GSSG when the composition is stored or used, or may be oxidized to become GSSG after the composition is supplied to a plant. Note that a method of oxidizing GSH to GSSG is not particularly limited. For example, GSH can be easily changed to GSSG via air oxidation. Alternatively, various kinds of conventionally well-known artificial methods may be used to change GSH to GSSG.

The composition of the present invention may contain another component unless effects of the amino acid content promoting agent are not lost. For example, the composition of the present invention may be dissolved in water, an conventionally well-known liquid carrier, or the like and be provided in the form of liquid, emulsion, gel, or the like. Examples of such a liquid carrier encompass: aromatic hydrocarbons such as xylene; alcohols such as ethanol and ethylene glycol; ketones such as acetone; ethers such as dioxane and tetrahydrofuran; and others such as dimethyl formamide, dimethyl sulfoxide, and acetonitrile, however, the examples are not limited thereto. Further, the composition of the present invention may be a solid, powder, or the like in which the amino acid content promoting agent is carried by a solid carrier component. Examples of such a solid carrier component encompass inorganic substances such as talc, clay, vermiculite, diatomaceous earth, kaolin, calcium carbonate, calcium hydroxide, white clay, and silica gel; and organic substances such as flour and starch, however, the examples are not limited thereto. The composition of the present invention may contain other adjuvants as appropriate. Examples of such an adjuvant encompass: cationic surface-active agents such as alkyl sulfuric ester, alkyl sulfonates, alkylaryl sulfonates, dialkyl sulfosuccinate; cationic surface-active agents such as salts of higher aliphatic amines; anionic surface-active agents such as polyoxyethylene glycol alkyl ethers, polyoxyethylene glycol acyl esters, polyoxyethylene glycol polyalcohol acyl esters, and cellulose derivatives; thickeners such as gelatin, casein, and gum arabic; and others such as bulking agents and binding agents.

As described in Examples below, forms of the composition of the present invention are not particularly limited, and can be in the form of liquid, tablets, powders, or granules. For example, in a case where the composition is provided in the liquid form, the composition of the present invention may be contained in a medium or the like to be used to grow a plant, or may be scattered over, dropped toward, or applied to a part (such as growing point, bud, leaf, and stem) of or a whole plant. Note that the "medium" for use in the present specification encompass soil and soil conditioners.

In a case where the composition of the present invention is provided in the form of tablets, powders, or granules, the composition may be contained in a medium to be used to grow a plant, or, in a case where a plant is grown in water, the composition may be placed in water and be gradually dissolved. The composition may be provided as a solid or the like so as to be dissolved in water and be dissolved when the composition is used. The composition of the present invention may be also mixed with chemical agents such as a conventionally well-known fertilizer and a phytohormone and be provided to a plant.

Note that, as described in Examples below, a plant which has been cultivated while having been supplied with the composition of the present invention has an amino acid content remarkably higher than a plant which has been cultivated while having been supplied with a nitrogen fertilizer (ammonium nitrate). This indicates that it is not always necessary to use a conventional nitrogen fertilizer in addition in order to increase the amino acid content. As described above, the composition of the present invention do not have to contain a nitrogen source.

The present invention further provides a kit (hereinafter, referred to also as "kit of the present invention") for increasing an amino acid content in a plant. The kit of the present invention is only necessary to include the composition (composition of the present invention) containing the amino acid content promoting agent or the amino acid content promoting agent. Further, the kit of the present invention may be used to produce a plant having an increased amino acid content.

The kit of the present invention may include another component in addition to those substances. The amino acid content promoting agent and the another component may be provided in a single container or in separate containers while having appropriate volumes and/or forms. The kid may further include a tool, medium, etc. to be used to grow a plant. Further, in order to achieve the use to increase an amino acid content in a plant, the kit of the present invention preferably include instructions in which procedures for increasing an amino acid content in a plant or procedures for producing a plant having an increased amino acid content are described. The "instructions" may be written in paper or other media, may be printed, or may be stored in an electronic medium such as magnetic tape, computer readable disk, tape, and CD-ROM. The kit of the present invention may be used for constituting the above composition. The kit may separately include the substances contained in the composition, or may separately include the composition and another component.

A timing for supplying the composition or the amino acid content promoting agent of the present invention to a plant is not particularly limited, and the composition or the amino acid content promoting agent of the present invention may be supplied under the condition that a plant can always take up the amino acid content promoting agent, or the composition or the amino acid content promoting agent of the present invention may be supplied under the condition that a plant can take up the amino acid content promoting agent intermittently (e.g., condition of supplying the amino acid content promoting agent once a week or twice a week) during a cultivation period. Alternatively, the composition or the amino acid content promoting agent of the present invention may be supplied during a particular growing season. By supplying the composition or the amino acid content promoting agent of the present invention intermittently, an amount of the amino acid content promoting agent used can be reduced, thereby reducing a cost for plant cultivation. Note that, in a case where the composition or the amino acid content promoting agent of the present invention are supplied intermittently, such supply is preferably carried out at regular intervals, however, is not limited thereto, and may be carried out at irregular intervals. For example, the composition or the amino acid content promoting agent of the present invention may be provided since a seed of a plant is seeded. Specifically, in a case where the composition or the amino acid content promoting agent of the present invention is provided to a plant which will be ready for harvest in about 2 months to a time period of slightly less than 6 months after seeding, the composition or the amino acid content promoting agent of the present invention may be provided at a day at which a seed of the plant is seeded, and may be provided at regular intervals preferably during a period from a day at which the seed is seeded to 4 weeks from the seeding, more preferably during a period from the day at which the seed is seeded to 7 weeks from the seeding, and further preferably during a period from the day at which the seed is seeded to a day at which the plant is harvested. In this case, while an interval at which the composition or the amino acid content promoting agent of the present invention is provided is not particularly limited, the interval is preferably once a week to 4 times a week, and more preferably twice to third times a week.

A time interval at which the composition or the amino acid content promoting agent of the present invention is supplied is not particularly limited, and may be determined on the basis of a concentration of the amino acid content promoting agent to be supplied, a plant to which the composition or the amino acid content promoting agent of the present invention is applied (subject plant), a timing when the composition or the amino acid content promoting agent of the present invention is supplied, etc. Generally, in the event that a subject plant is a herbaceous plant, the composition or the amino acid content promoting agent of the present invention is preferably supplied once a week to twice a week or at the same time as an additional manuring timing.

In the case that a crop having an increased amino acid content is seeds and fruits, it is preferable to supply the composition or the amino acid content promoting agent of the present invention to plants before and after a transition period from a vegetative stage to a reproductive stage (including the transition period from the vegetative stage to the reproductive stage), after a flower bud formation stage thereafter, or a period during which flow of the amino acid content to a crop of interest occurs. With this, the composition or the amino acid content promoting agent of the present invention is used only during a particular period, thereby reducing a cost for plant cultivation.

In a case where the composition or the amino acid content promoting agent of the present invention is supplied during a particular period, the composition or the amino acid content promoting agent of the present invention may be supplied during a certain period of the particular period under the condition that a plant can always take up the amino acid content promoting agent, or may be supplied during a certain period of the particular period under the condition that a plant can intermittently take up the amino acid content promoting agent. By intermittently supplying the composition or the amino acid content promoting agent of the present invention during the certain period of the particular period, it is possible to further reduce a cost for plant cultivation.

An amount of the amino acid content promoting agent to be supplied is not particularly limited, and may be determined in accordance with the kind of plant as appropriate. In a case where GSSG is supplied as the amino acid content promoting agent, an amount of GSSG supplied per individual during a cultivation period is preferably 0.02 mmol or more but 0.5 mmol or less, and more preferably 0.05 mmol or more but 0.5 mmol or less. Further, it is more preferable to use the amino acid content promoting agent supplied as described above within a range of the use concentration, however, the concentration is not limited thereto.

The composition of the present invention may be supplied during a predetermined period after a plant is grown to a certain degree, for example, after a seed is seeded and grown to a seedling. For example, in a case where the composition of the present invention is supplied to a grass such as sweet corn, the composition of the present invention may be supplied after a seedling is grown. In this case, a medium in which the seedling thus grown is planted may contain the composition of the present invention in advance, or the composition of the present invention may be supplied to the medium at regular intervals after the seedling is planted in the medium. In a case where the composition of the present invention is provided to a medium after a seedling is transplanted, a specific supply timing is not particularly limited, however, for example, such provision is preferably once a week to 4 times a week, and more preferably twice a week to 3 times a week during a period after the seedling is transplanted but before the seedling is harvested. An amount of the composition of the present invention used is not particularly limited, and may be determined in accordance with the kind of plant.

Further, a timing of providing the composition or the amino acid content promoting agent of the present invention may be determined by counting backwards from a harvesting stage. For example, provision of the composition or the amino acid content promoting agent of the present invention may be started from 10 days or 20 days before the harvesting stage. The harvesting stage herein indicates a harvesting stage of seeds in a case where the seeds are a crop, and indicates leaves in a case where the leaves are a crop, i.e., any type of crops are included.

In a case where seeds or fruits are a crop, a timing of providing the composition or the amino acid content promoting agent of the present invention may be determined on the basis of a timing at which plants bear flowers. For example, the composition or the amino acid content promoting agent of the present invention may be supplied during a period of a bud, after a petal is fell, during a period between a bud and ripening of a fruit, during a period after a flower is bloomed but before a fruit is ripened, or during a period after a petal is fell but before a fruit is ripened. The composition or the amino acid content promoting agent of the present invention may be supplied to an inflorescence.

Note that, in a case where the composition of the present invention is used for the purpose of preparing a solution containing the amino acid content promoting agent successfully, the composition of the present invention is preferable in the form of tablets, powders, or granules. Further, it is preferable that the amino acid content promoting agent be contained in the composition so that a resultant concentration of the amino acid content promoting agent in the solution thus obtained falls within the above range.

As described above, in a case where the composition or the amino acid content promoting agent of the present invention is supplied during a cultivation period, chemical agents such as a fertilizer and/or phytohormone mixed with the composition may be supplied to a plant as described above. In this case, a timing of providing a mixture of the fertilizer etc. and the composition is not particularly limited, and such providing may be carried out in accordance with the above examples, or may be carried out in accordance with a preferable timing of providing the fertilizer etc.

In the present specification, the "plant" means a whole plant, plant organs (e.g., leaf, petal, stem, root, seed, etc.), plant tissues (e.g., epidermis, phloem, parenchyma, xylem, vascular bundle, palisade tissue, spongy tissue, etc.), plant cultured cell, various forms of plant cell (e.g., suspended cultured cell), protoplast, slice of leaf, callus, etc.

The present invention is not limited to a particular subject plant, and the present invention is applicable to all plants such as various monocotyledons, dicotyledons, trees, etc. Examples of monocotyledons encompass Lemnaceae plants including *Spirodela* plants (great duckweed) and *Lemna* (duckweed, star duckweed); Orchidaceae including *Cattleya, Cymbidium, Dendrobium, Phalaenopsis, Vanda, Paphiopedilum,* and *Oncidium*; others such as Typhaceae, Sparganiaceae, Potamogetonaceae, Najadaceae, Najadaceae, Alismataceae, Hydrocharitaceae, Triuridaceae, Gramineae (corns such as sweet corn), Cyperaceae, Palmae, Araceae, Eriocaulaceae, Commelinaceae, Pontederiaceae, Juncaceae, Stemonaceae, Liliaceae, Amaryllidaceae, Dioscoreaceae, Iridaceae, Musaceae, Zingiberaceae, Cannaceae, and Burmanniaceae.

Examples of dicotyledons encompass: Convolvulaceae such as *Pharbitis* (morning glory), *Calystegia* (Japanese bindweed, bindweed, see bells), *Ipomoea* (beach morning glory, sweet potato), and *Cuscuta* (dodder (such as *C. japonica* and *C. australis*)); Caryophyllaceae including *Dianthus* (carnation etc.), *Stellaria, Minuartia, Cerastium, Sagina, Arenaria, Moehringia, Pseudostellaria, Honckenya, Spergula, Spergularia, Silene, Lychnis, Melandryum,* and *Cucubalus*; and others such as Casuarinaceae, Saururaceae, Piperaceae, Chloranthaceae, Salicaceae, Myricaceae, Juglandaceae, Betulaceae, Fagaceae, Ulmaceae, Moraceae, Urticaceae, Podostemaceae, Proteaceae, Olacaceae, Santalaceae, Loranthaceae, Aristolochiaceae, Mitrastemonaceae, Balanophoraceae, Polygonaceae, Chenopodiaceae, Amaranthaceae, Nyctaginaceae, Theligonaceae, Phytolaccaceae, Aizoaceae, Portulacaceae, Magnoliaceae, Trochodendraceae, Cercidiphyllaceae, Nymphaeaceae, Ceratophyllaceae, Ranunculaceae, Lardizabalaceae, Berberidaceae, Menispermaceae, Calycanthaceae, Lauraceae, Papaveraceae, Capparaceae, Cruciferae, Droseraceae, Nepenthaceae, Crassulaceae, Saxifragaceae, Pittosporaceae, Hamamelidaceae, Platanaceae, Rosaceae, Leguminosae, Oxialidaceae, Geraniaceae, Linaceae, Zygophyllaceae, Rutaceae, Simaroubaceae, Meliaceae, Polygalaceae, Euphorbiaceae, Callitrichaceae, Buxaceae, Empetraceae, Coriariaceae, Anacardiaceae, Aquifoliaceae, Celastraceae, Staphyleaceae, Icacinaceae, Aceraceae, Hippocastanaceae, Sapindaceae, Sabiaceae, Balsaminaiceae, Balsaminaiceae, Vitaceae, Elaeocarpaceae, Tiliaceae, Malvaceae, Sterculiaceae, Actinidiaceae, Theaceae, Guttiferae, Elatinaceae, Tamaricaceae, Violaceae, Flacourtiaceae, Stachyuraceae, Passifloraceae, Begoniaceae, Cactaceae, Thymelaeaceae, Elaeagnaceae, Lythraceae, Punicaceae, Rhizophoraceae, Alangiaceae, Melastomataceae, Trapaceae, Onagraceae, Haloragaceae, Hippuridaceae, Araliaceae, Umbelliferae, Cornaceae, Diapensiaceae, Clethraceae, Pyrolaceae, Ericaceae, Myrsinaceae, Primulaceae, Plumbaginaceae, Ebenaceae, Symplocaceae, Styracaceae, Styracaceae, Buddlejaceae, Gentianaceae, Apocynaceae, Asclepiadaceae, Polemoniaceae, Boraginaceae, Verbenaceae, Labiatae, Solanaceae (tomato etc.), Scrophulariaceae, Bignoniaceae, Pedaliaceae, Orobanchaceae, Gesneriaceae, Lentibulariaceae, Acanthaceae, Myoporaceae, Phrymaceae, Phrymaceae, Rubiaceae, Caprifoliaceae, Adoxaceae, Valerianaceae, Dipsacaceae, Cucurbitaceae, Campanulaceae, and Compositae. The plant to which the present invention is applied may be not only the wild plants cited above, but also variants or transformants thereof.

Note that, as described in Examples below, a part having an increased amino acid content in a plant is not particularly limited, and the part may be a crop or other parts (e.g., organs or tissues used only for extracting an amino acid). The "crop" indicates a food part in a plant, and is, for example, a fruit in a case where the fruit of the plant is edible, a seed in a case where the seed of the plant is edible, a stem in a case where the stem of the plant is edible, a root in a case where the root of the plant is edible, a flower in a case where the flower of the plant is edible, and a leaf in a case where the leaf of the plant is edible, however, the "crop" is not limited thereto.

[3. Method of Increasing Amino Acid Content in Plant and Method of Producing Plant Having Increased Amino Acid Content]

The present invention provides a method of increasing an amino acid content in a plant (hereinafter, referred to as "method of the present invention"). The method of the present invention is only necessary to include the step of supplying the composition or the amino acid content promoting agent of the present invention to a plant.

It is possible to cause a plant to take up the amino acid content promoting agent by bringing the plant into contact with the amino acid content promoting agent, and therefore the above step can be a step of bringing the amino acid content promoting agent into contact with a plant of interest or a step of causing a plant of interest to take up the amino acid content promoting agent. A procedure of causing a plant to take up the amino acid content promoting agent is not particularly limited. For example, the composition or the amino acid content promoting agent of the present invention may be taken up through a root of a plant by cultivating the plant in a medium (including soil and soil conditioner) containing the composition or the amino acid content promoting agent of the present invention, or the composition or the amino acid content promoting agent of the present invention may be provided, sprayed, applied to a plant in the form of granules or as a liquid fertilizer during a plant cultivation period so that the plant can take up the amino acid content promoting agent. The plant may be cultivated by providing, in a medium, an absorbent such as ion-exchange resin which has absorbed the composition or the amino acid content promoting agent of the present invention, for example, by burying the absorbent in a soil. That is, the method of the present invention further includes the step of cultivating a plant in the presence of the amino acid content promoting agent. Note that a specific procedure of the step of the method of the present invention only needs to be inconformity to a usage mode of the composition or the amino acid content promoting agent of the present invention as described above.

The amino acid content promoting agent to be supplied may have a high concentration or a low concentration provided that the concentration can increase the amino acid content in a plant, and a desired effect can be obtained by appropriately determining an interval, a timing, a period, etc. at/during which the amino acid content promoting agent is provided. For example, a range of the concentration of the amino acid content promoting agent to be in contact with a plant is preferably 0.2 mM to 5 mM, more preferably 0.5 mM to 5 mM, further preferably 1 mM to 5 mM, and further more preferably 2 mM to 5 mM.

In a case where a total amount of the amino acid content promoting agent provided to a plant falls within a particular range during a cultivation period, an amino acid content in the plant can be increased. The total amount of the amino acid content promoting agent to be supplied to the plant during the cultivation period can be converted to an amount of GSSG. For example, an amount of GSSG used during a cultivation period of 4 weeks falls preferably within a range of 12.5 mg to 300 mg per individual plant and a range of 60 mg to 1450 mg per liter of soil. While a period during which a plant is cultivated while GSSG is being supplied is not particularly limited, however, the period is preferably from 4 weeks (28 days) before a harvesting stage to the harvesting stage. Note that the amino acid content promoting agent has an effect in a smaller amount in a case where an absorbent or the like of the amino acid content promoting agent is buried in a soil and used, as compared with an amount of the amino acid content promoting agent supplied as a liquid fertilizer to a soil or a plant, because a contact period with respect to a plant body becomes longer.

As a matter of course, the amino acid content is increased in a plant to which the method of the present invention is applied. In order to confirm that, the method of the present invention may further include the step of measuring an amino acid content in a plant to which the amino acid content promoting agent is supplied. Further, as described in Example 5 below, an amino acid content in a crop of interest of a plant is increased by the method of the present invention. In order to confirm that, the method of the present invention may further include the step of measuring the amino acid content in a crop of interest of a plant to which the amino acid content promoting agent is supplied. Note that a method of measuring the amino acid content in a plant may be carried out in accordance with conventionally well-known procedures, or may be carried out in accordance with procedures described in the Examples below.

In order to control the effect of the present invention (i.e., effect of increasing the amino acid content in a plant), the method of the present invention may further includes the step of controlling a light condition at a harvesting stage of a plant to which the present invention has been applied. As described in Examples below, by combining supply of the amino acid content promoting agent with photoirradiation before harvesting, there are an amino acid whose content in a crop is increased and an amino acid whose content in a crop is decreased. With this configuration, it is possible to increase a amino acid content of interest successfully, or to regulate a content ratio of an amino acid in a crop to a desired value. Note that control of the light condition may be a change from a light condition to a dark condition, may be a change from a dark condition to a light condition, or may be a change in intensity of the light condition, provided that the control is carried out before a crop is harvested. A start timing of control and a control period are not particularly limited provided that the crop is harvested during a period after 8 or more hours pass from start of the control but before the control is completed. The start of the control may be before or after the supply of the amino acid content promoting agent to a plant, and it is preferable to start the control of the amino acid content promoting agent after the amino acid content promoting agent is supplied.

In order to control effect of the present invention (i.e., effect of increasing an amino acid content in a plant), the method of the present invention may further include the step of controlling a temperature condition during a cultivation period of a plant to which the present invention is applied. As described in Examples below, even if a plant is not grown within the most suitable range for growth of the plant, it is possible to increase an amino acid content in the plant by supplying the amino acid content promoting agent and controlling the temperature condition. Note that the control of the temperature condition may be a change from a high temperature condition to a low temperature condition or a change from the low temperature condition to the high temperature condition, and a start timing and a control period are not particularly limited provided that the control is started after seeding (preferably, germinating) and a crop is harvested before completion of the control. The control may be started before or after the amino acid content promoting agent is supplied to the plant, but is preferably started after the amino acid content promoting agent is supplied.

The present invention further provides a method of producing having an increased amino acid content (hereinafter, referred to as "producing method of the present invention"). In the producing method of the present invention, the method of the present invention described above is used, and is only necessary to include the steps of supplying the composition or the amino acid content promoting agent of the present invention to a plant and cultivating the plant in the presence of the amino acid content promoting agent. Further, the producing method of the present invention preferably further includes the step of measuring the amino acid content in the plant to which the amino acid content promoting agent is supplied, and also preferably includes the step of measuring the amino acid content in a crop of interest of the plant to which the amino acid content promoting agent is supplied.

Further, in order to confirm that an amino acid content in a plant produced by the producing method of the present invention is increased, it is more preferable that the producing method of the present invention further include the step of selecting a plant having an increased amino acid content more than that of a plant cultivated in the absence of the amino acid content promoting agent. With this, it is possible to select a plant of interest successfully.

It is also possible to know whether or not a plant is produced by the producing method of the present invention on the basis of a production amount of metabolite or an expression level of genes. That is, in order to successfully select a plant produced by the producing method of the present invention, the producing method of the present invention may include the step of selecting a plant having a profile which is characteristic in a plant cultivated in the presence of the amino acid content promoting agent as described below, and the profile used herein may be a metabolite production amount profile which is profile of a production amount of metabolite or a gene expression profile which is a profile of an expression level of a gene. In this case, a plant of interest can be selected by comparing a metabolite production amount profile or a gene expression profile obtained in advance with those profiles of the plant, however, the producing method of the present invention may further include the step of obtaining any one of the metabolite production amount profile and the gene expression profile in a plant.

A method of obtaining a metabolite production amount profile is not particularly limited, and a conventionally well-known method for measuring an amount of metabolite can be used, and, for example, it is preferable to carry out comprehensive analysis such as metabolome analysis. For example, a metabolite production amount profile can be obtained as follows: tendencies of a change in production amounts of respective metabolites of samples measured with use of CE-TOFMS are expressed in numbers; the multiple metabolites are classified in accordance with patterns of the production amounts thereof by using hierarchical cluster analysis (HCA) for dividing analogous results into groups; and a result of such classification is shown as a tree diagram (see FIG. 4). Further, by showing a degree of a change in the form of Haet Map, it is possible to visualize the classification of the metabolites in a manner more easy to understand visually. The tree diagram and the Heat Map obtained as described above have a unique pattern for each condition to be employed, and, for example, it is possible to easily differentiate a plant body obtained by the method of the present invention from a plant body under a control condition.

The present invention further provides a plant having an increased amino acid content (hereinafter, referred to as "plant of the present invention"). The plant of the present invention is a plant obtained by the producing method of the present invention. The plant of the present invention is not particularly limited provided that the plant is a plant cited as the "plant to which the present invention is applied" above, the plant may be a land plant or an aquatic plant, and an preferable aquatic plant is algae.

As described above, the plant of the present invention can be specified by comparing a metabolite production amount profile obtained with use of metabolome analysis or the like. In a case of using the amino acid content promoting agent, as shown in, for example, FIG. 4, a metabolite production amount profile in a plant which has been cultivated while having been supplied with the amino acid content promoting agent (e.g., GSSG) (such a metabolite production amount profile will be referred to also as "metabolite production amount profile of the present invention") is different from a metabolite production amount profile obtained from a plant which has been cultivated by another method. Therefore, it is possible to determine easily and clearly whether or not a plant is obtained by the producing method of the present invention by obtaining a metabolite production amount profile of the plant to be examined and comparing the metabolite production amount profile thereof with the metabolite production amount profile of the present invention obtained in advance.

In addition to the method of checking the metabolite production amount profile, for example, it is also possible to determine easily and clearly whether or not a plant is obtained by the producing method of the present invention by obtaining a gene expression profile with use of a DNA microarray or the like and comparing the gene expression profile. In a case of using the amino acid content promoting agent, for example, a gene expression profile of a plant which has been cultivated while having been supplied with the amino acid content promoting agent (e.g., GSSG) (such a gene expression profile will be referred to as a gene expression profile of the present invention) can be different from a gene expression profile obtained from a plant which has been cultivated by the another method. Therefore, it is possible to determine easily and clearly whether or not a plant is a plant obtained by the producing method of the present invention by obtaining the gene expression profile and comparing the gene expression profile with the gene expression profile of the present invention obtained in advance. Further, as another procedure, it is possible to determine whether or not GSSG is supplied to be examined by comparing a two-dimensional electrophoresis pattern of glutathione-binding protein with a pattern change of a two-dimensional electrophoresis pattern thereof which has been obtained in advance. It is also possible to confirm that a plant of the present invention is not a plant obtained by transgenes is (transformation) by examining a gene of interest in the plant with use of a PCR method, a southern hybridization method, a northern hybridization method, or the like. As a further another method, by measuring at least one of an amount and a ratio of the amino acid content promoting agent in an plant, it is possible to clearly differentiate a plant obtained by the method of the present invention from a plant obtained by a method other than the method of the present invention. Those methods may be carried out solely or a plurality of methods may be carried out in combination. By combining the plurality of methods, it is possible to differentiate more clearly a plant of the present invention from a plant obtained a method other than the method of the present invention.

The following is Examples, and embodiments of the present invention will be describe below in more detail. All publications referred to herein are incorporated by reference herein in their entireties in the present specification.

Example 1

1: Effect of Glutathione on Total Free Amino Acid Content in *Arabidopsis*

*Arabidopsis* was grown at 22° C. under a photoperiodic condition of a light period of 16 hours/a dark period of 8 hours at a light intensity of 100 μE/m². A growth experiment was performed with a medium, in which a soil had been formed by placing vermiculite (Asahi industrial corporation) as a lower layer, KUREHA seedling raising soil (KUREHA CORPORATION) as a middle layer, and vermiculite (Asahi industrial corporation) as an upper layer at a ratio of 2:1:1 in lamination.

In this experiment, only water (Cont.), 1 mM of an oxidized glutathione (GSSG) solution, 2 mM of a reduced glutathione (GSH) solution, or 3 mM of ammonium nitrate ($NH_4NO_3$) were provided to plants. Specifically, 3 individuals were put into each pot having about 65 mM (W)×65 mM (D)×50 mM (H), and 25 mL of each solution is provided to roots of each pot once a week.

In order to measure an amino acid content, a plant after 4 weeks from seeding and a plant after 5 weeks from seeding were used. Note that a leaf (or a terrestrial part) was measured as a sample in a cation mode and an anion mode of CE-TOFMS (capillary electrophoresis-time-of-flight mass spectrometry: Agilent CE-TOFMS system (Agilent technologies)). By comparing a detected peak with database on the basis of m/Z and a migration period, an amino acid was searched, identified, and quantified.

The sample for use in the CE-TOFMS was prepared as follows. First, 500 μL of a methanol solution including a leaf sample and containing 50 μM of an internal standard substance was introduced into a crushing tube, was frozen with use of liquid nitrogen, and was crushed with use of a desktop-type crusher. Then, 500 μL of chloroform and 200 μL of Milli-Q water were added to the resultant and were stirred, and were then centrifuged (2300×g, 4° C., 5 minutes). After such centrifugation, an aqueous phase was transferred to 400 μL of a ultrafiltration tube (MILLIPORE, Ultrafree-MC Centrifugal Filter Units 5 kDa). This aqueous phase thus transferred was centrifuged (9100×g, 4° C., 120 minutes), and an aqueous phase was subjected to an ultrafiltration process. A resultant filtrate was dried, was dissolved in 50 μL of Milli-Q water, and was measured.

Results of amino acid contents quantified with CE-TOFMS are shown in FIG. 1. As shown in (a) of FIG. 1, comparing total free amino acid contents of plants after 4 weeks from seeding, total free amino acid contents under GSSG treatment (2) and GSH treatment (3) were about 2.8 times and about 2.9 times as much as a total free amino acid content under control condition (1) to which only water had been provided, i.e., the total free amino acid contents under the GSSG treatment (2) and the GSH treatment (3) were remarkably increased. All amino acid contents under ammonium nitrate treatment (4) whose nitrogen source is ammonium nitrate were not increased.

Total free amino acid contents of plants after 5 weeks from seeding were less than those of the plants after 4 weeks from seeding under all conditions, and, as shown in (b) of FIG. 1, the total free amino acid contents under the GSSG treatment (2) and the GSH treatment (3) were about 2.0 times and about 2.4 times as much as the total free amino acid content under the control condition (1) to which only water was provided, i.e., the total free amino acid contents under the GSSG treatment (2) and the GSH treatment (3) were remarkably increased. The total free amino acid content under the ammonium nitrate treatment (4) whose nitrogen source was ammonium nitrate was slightly increased (about 1.37 times) unlike the total free amino acid content of the plant after 4 weeks from seeding, however, was clearly less than that under the glutathione treatment.

[2: Effect of Glutathione on Each Free Amino Acid Content in *Arabidopsis*]

Figure 2:
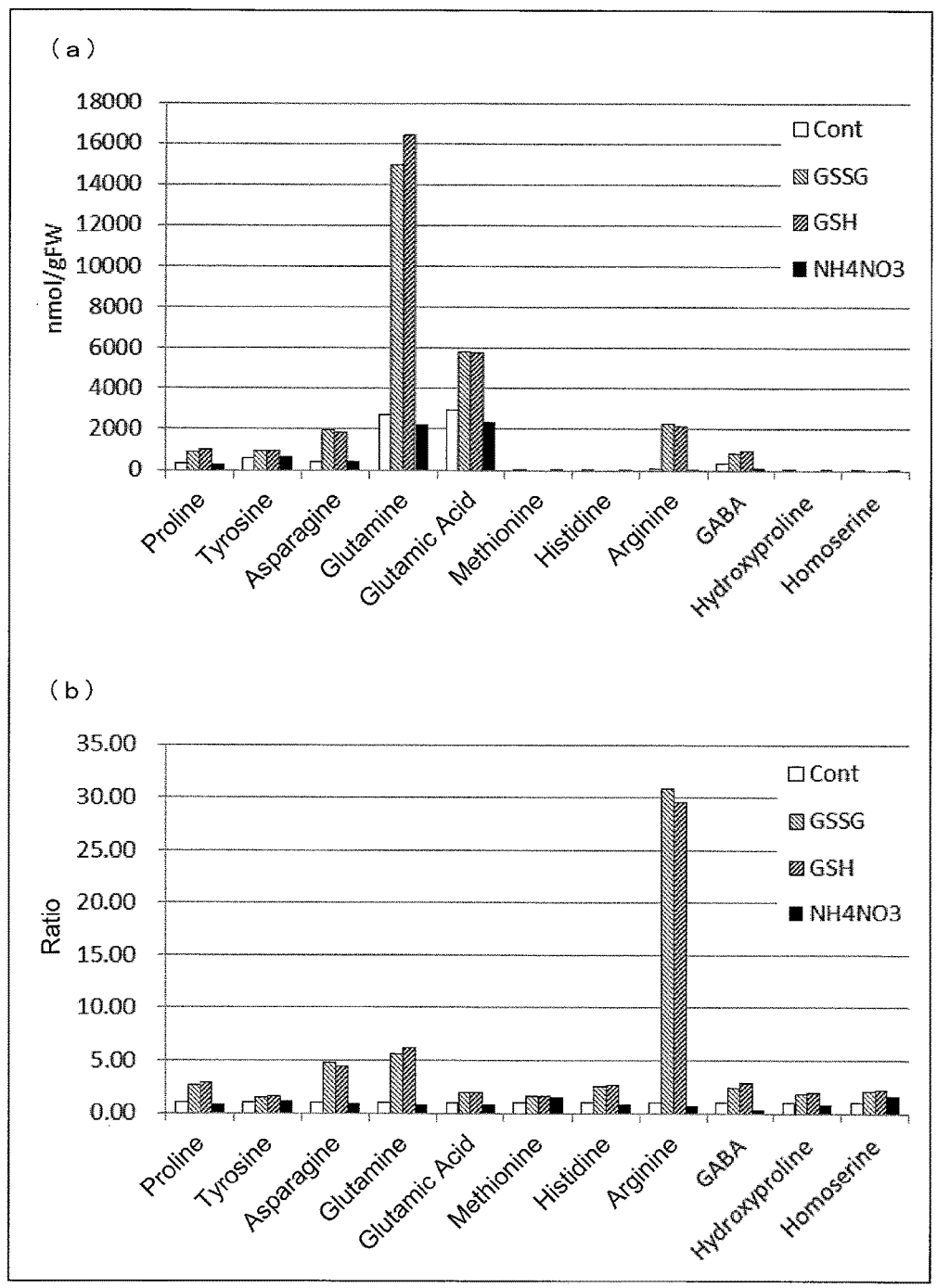
FIG. 2 shows a graph (a) showing a quantity per fresh weight of various amino acids (proline, tyrosine, asparagine, glutamine, glutamic acid, methionine, histidine, arginine, GABA, hydroxyproline, homoserine) contained in *Arabidopsis* which has been grown under various cultivation conditions after 4 weeks from seeding, and shows a ratio (b) assuming that such a quantity under a control condition (Cont.) is 1.

(a) of FIG. 2 shows quantities of free amino acids of *Arabidopsis* grown for 4 weeks from seeding in the presence of an amino acid content promoting agent, which was the same condition as the condition above, and quantified with use of CE-TOFMS. Absolute quantities of respective amino acids are greatly different, however, every amino acid shown in FIG. 2 was greatly increased under the GSSG treatment and under the GSH treatment in comparison with those under the control condition (Cont.). As shown in (b) of FIG. 2, contents of some amino acids were remarkably increased (about 1.5 times to about 30 times). Specifically, contents of proline, tyrosine, asparagine, glutamine, glutamic acid, methionine, histidine, and arginine were clearly increased, and, contents of asparagine, glutamine, and arginine were remarkably increased. Amino acids other than main α-amino acids constituting proteins such as GABA, hydroxyproline, and homoserine were also increased. Note that, in a case where nitrogen fertilizer ($NH_4NO_3$) was added, amino acid contents were scarcely increased.

Figure 3:
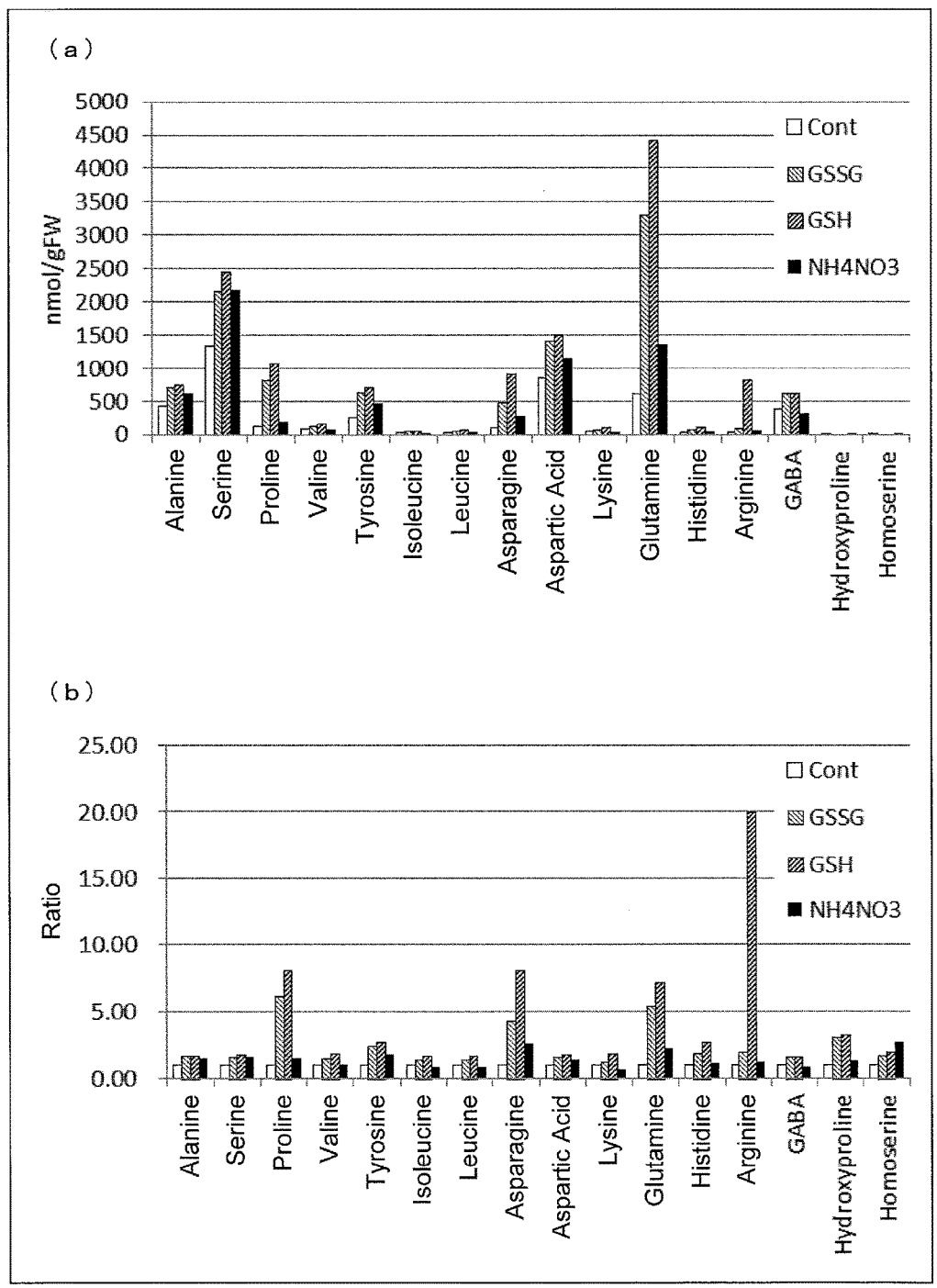
FIG. 3 shows a graph (a) showing a quantity per fresh weight of various amino acids (alanine, serine, proline, valine, tyrosine, isoleucine, leucine, asparagine, aspartic acid, glutamine, histidine, arginine, GABA, hydroxyproline, homoserine) contained in *Arabidopsis* which has been grown under various cultivation conditions after 5 weeks from seeding, and a ratio (b) assuming that such a quantity under a control condition (Cont.) is 1.

(a) of FIG. 3 shows quantities of free amino acids of *Arabidopsis* grown for 5 weeks from seeding in the presence of an amino acid content promoting agent which was the same condition as the condition above and quantified with use of CE-TOFMS. Absolute quantities of respective amino acids are greatly different, however, every amino acid shown in FIG. 3 was greatly increased under the GSSG treatment and the GSH treatment in comparison with those under the control condition (Cont.). As shown in (b) of FIG. 3, contents of some amino acids were remarkably increased (about 1.5 times to about 20 times). Specifically, contents of alanine, serine, proline, valine, tyrosine, isoleucine, leucine, asparagine, lysine, glutamine, histidine, and arginine were clearly increased, and, contents of proline, asparagine, glutamine, and arginine were remarkably increased. Amino acids other than main α amino acids constituting proteins such as GABA, hydroxyproline, and homoserine were also increased. Note that, in a case where nitrogen fertilizer ($NH_4NO_3$) was added, amino acid contents were scarcely increased, as compared with those of the control condition.

[3: Effect of Glutathione on Metabolite Production Amount Profile of *Arabidopsis*]

Figure 4:
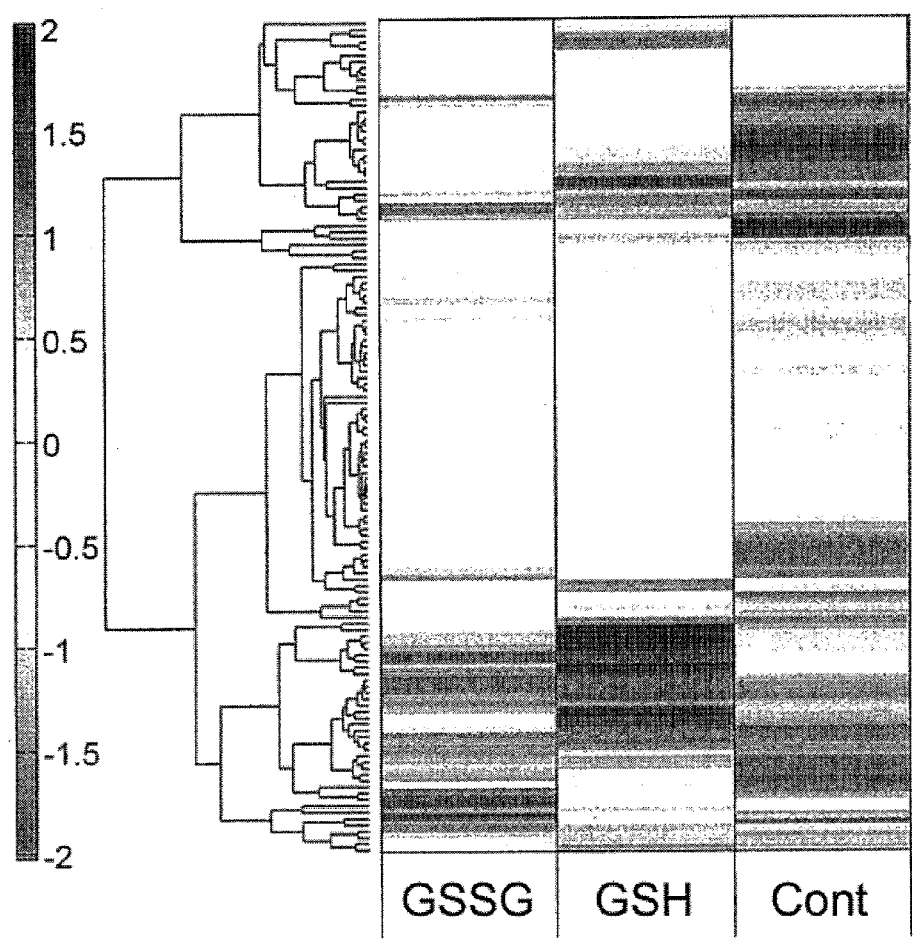
FIG. 4 is a view illustrating a change in production amount of a metabolite in *Arabidopsis* to which glutathione has been supplied.

FIG. 4 shows a result of analysis based on comparison between (i) a metabolite production amount profile of *Arabidopsis* which were prepared by adding oxidized glutathione (GSSG) and (ii) a metabolite production amount profile of *Arabidopsis* which were prepared by adding reduced glutathione (GSH), both of which metabolite production amount profiles were prepared at the same time as such amino acid analysis. The CE-TOFMS is capable of detecting various metabolites in addition to amino acids, and, as to 132 candidates herein obtained with use of the CE-TOFMS, tendencies of a change in metabolite quantities of samples thus measured were expressed in numbers, and were classified with use of hierarchical cluster analysis (HCA) for dividing similar results into groups. Production amounts of metabolites thus measured were classified as shown in a tree diagram of FIG. 4. Further, by showing a degree of a change in the form of Heat Map, it is possible to visualize the classification of the metabolites in a manner more easy to understand visually. The hierarchical cluster analysis and the Heat Map were prepared with use of SampleStat ver. 3.13 and PeakStat ver. 3.17 (both manufactured by Human Metabolome Technologies Inc.). A cluster of a metabolite characteristically increased under GSH treatment and a cluster characteristically increased under GSSG treatment are observed in FIG. 4. As described above, it was found that (i) production profiles of characteristic metabolites were obtained from a glutathione supply area and (ii) a plant whose amino acid was increased by glutathione treatment and an untreated plant were discriminable from each other.

Example 2

Control on Amino Acid Content Increase Effect of Glutathione by Light Condition

*Arabidopsis* which was grown under the cultivation conditions same as those of Example 1, amino acid contents of a leaf (L0) before photoirradiation (100 μE/m$^2$/s) and amino acid contents of a leaf (L8) after photoirradiation for 8 hours were compared with each other. Then, measurement of the amino acid contents were carried out in the same way as Example 1. Amino acid contents of leaves under a control condition (Cont.), leaves under 1 mM GSSG treatment, leaves under 2 mM GSH treatment, and leaves under 3 mM ammonium nitrate ($NH_4NO_3$) treatment are shown in FIG. 5.

Degrees of increase in each free amino acid content caused by glutathione were different depending on a light condition at the time of sampling. For example, as shown in FIG. 5, contents of β-alanine, glycine, proline, threonine, serine, and a glutamic acid in the leaf (L8) after the photoirradiation for 8 hours became larger than those in the leaf (L0) before the photoirradiation. Meanwhile, contents of leucine, valine, histidine, alanine, asparagine, an aspartic acid, arginine, and glutamine of the leaf before the photoirradiation (L0: dark condition) were higher than those of the leaf (L8) after the photoirradiation for 8 hours.

Figure 6:
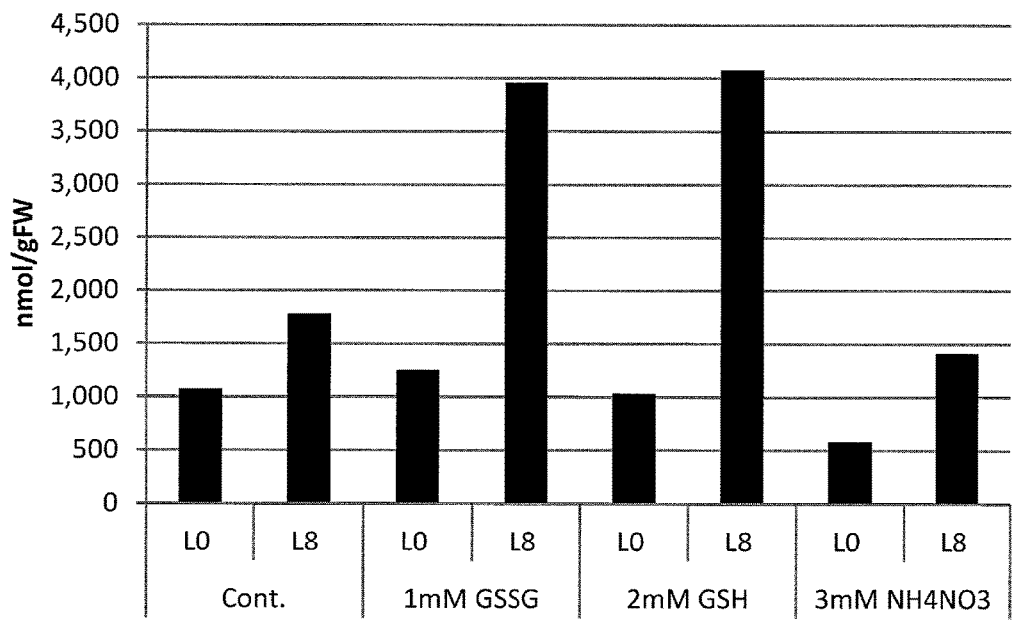
FIG. 6 is a view showing a serine content in each leaf of *Arabidopsis* to which glutathione has been supplied and which has been regulated in terms of a light condition before harvesting.

As an example of an amino acid whose content is increased by photoirradiation, a content (nmol/gFW) of serine is shown in FIG. 6. As shown in FIG. 6, by combining treatment of oxidized glutathione or reduced glutathione with photoirradiation, the serine content in a leaf was remarkably increased. Such a remarkable effect was not observed under a control condition and in an ammonium nitrate manuring area.

Figure 7:
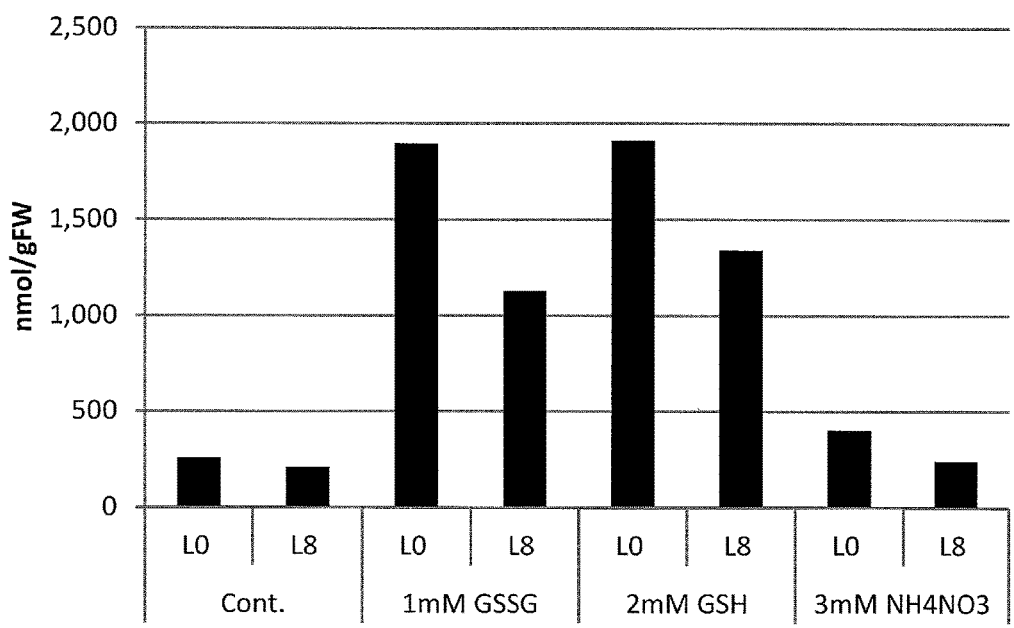
FIG. 7 is a view showing an asparagine content in each leaf of *Arabidopsis* to which glutathione has been supplied and which has been regulated in terms of a light condition before harvesting.

As an example of amino acid whose content is decreased by photoirradiation, a content (nmol/gFW) of asparagine is shown in FIG. 7. As shown in FIG. 7, the content in asparagine was largely increased by supplying oxidized glutathione or reduced glutathione, however, the effect was larger in a leaf before photoirradiation. Such an effect was not observed under the control condition and in the ammonium nitrate manuring area.

From those results, it was found that, by controlling not only supply of glutathione but also a light condition of a harvesting stage, an amino acid content was able to be further increased.

Example 3

Control on Amino Acid Content Increase Effect of Glutathione by Cultivation Temperature Condition

[1: Effect on Free Amino Acid Content by Cultivation Temperature Control of Spinach]

A cultivation condition of spinach, which was a vegetable of the goosefoot family (Chenopodioideae), supplied with glutathione was examined. After spinach was seeded, sprouts germinated to a similar extent were selected, were cultivated in an incubator (light period: 14 hours/dark period: 10 hours, light intensity: about 250 μE/m$^2$/s), and were sampled after 28 days. As a cultivation temperature, two types of a low temperature condition LT (Low Temperature: light period 20° C./dark period 15° C.) and a high temperature condition HT (High Temperature: light period 25° C./dark period 20° C.) were set. Note that an appropriate growth temperature range of spinach was a low temperature condition in this test, however, it is possible to grow spinach under the high temperature condition without any problem.

As a medium, a soil formed by placing vermiculite (Asahi industrial corporation) as a lower layer, KUREHA seedling raising soil (KUREHA CORPORATION) as a middle layer, and vermiculite (Asahi industrial corporation) as an upper layer at a ratio of 2:1:1 in lamination was used.

In this experiment, only water (Cont.), a 1 mM oxidized glutathione (GSSG) solution, and a 2 mM reduced glutathione (GSH) solution were provided to plants. Specifically, a single individual was put into each pot having about 65 mM (W)×65 mM (D)×50 mM (H), and 25 mL of each solution was provided to roots of each pot once a week.

In the same way as Example 1, a leaf (or a terrestrial part) was measured as a sample in a cation mode and an anion mode of CE-TOFMS (capillary electrophoresis-time-of-flight mass spectrometry: Agilent CE-TOFMS system (Agilent technologies)). By comparing a detected peak with database on the basis of m/Z and a migration period, an amino acid was searched, identified, and quantified. Results thus obtained are shown in FIG. 8 and FIG. 9.

Figure 8:
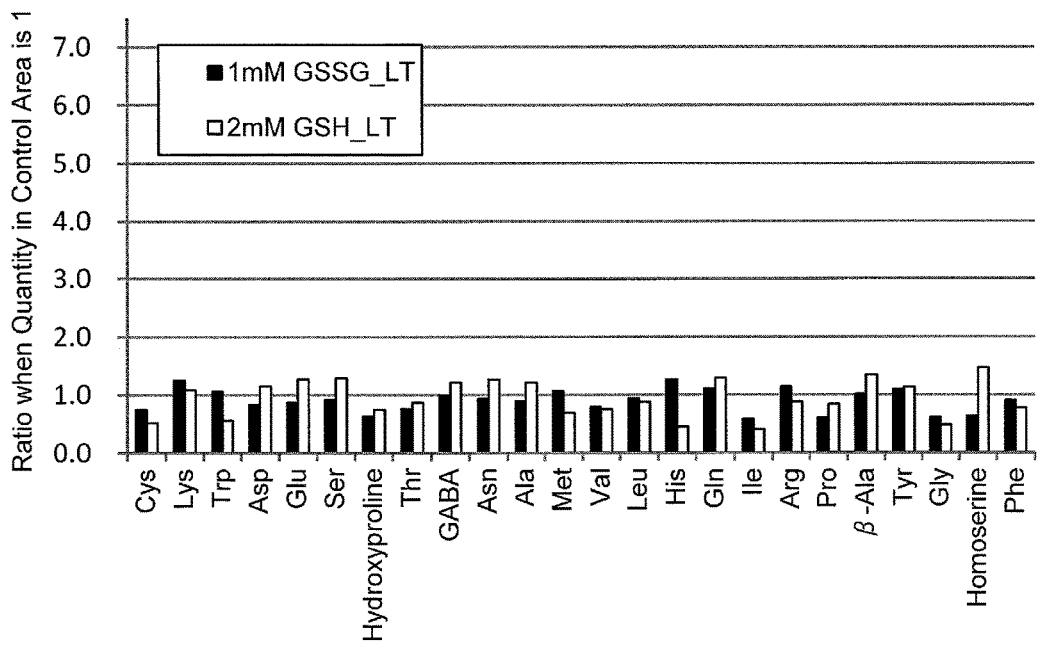
FIG. 8 is a view showing each free amino acid content in spinach to which glutathione has been supplied under a low temperature condition assuming that such a quantity under a control condition is 1.
Figure 9:
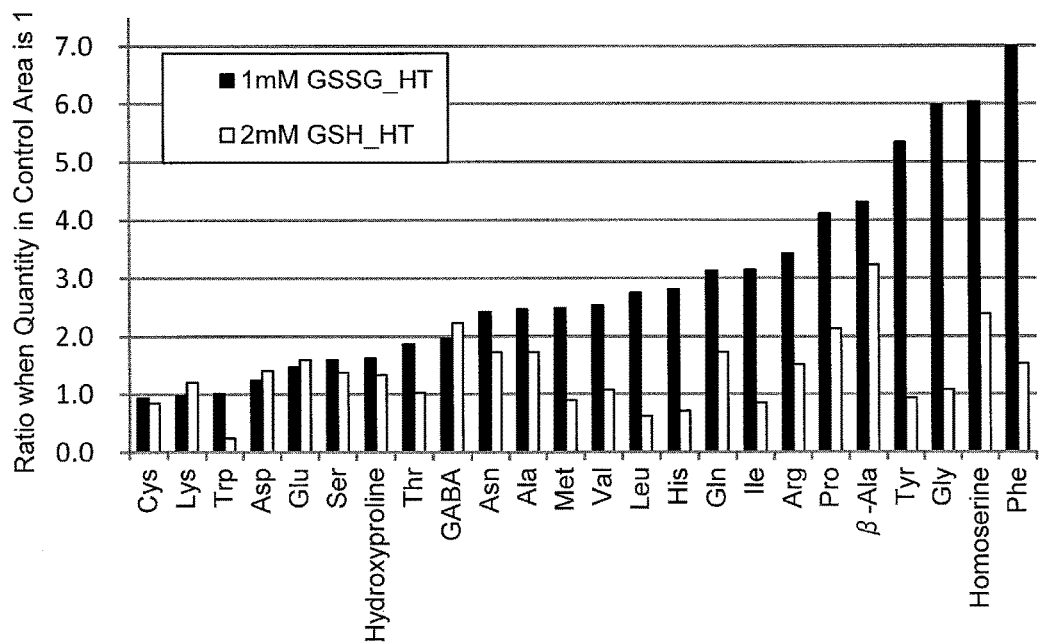
FIG. 9 is a view showing each free amino acid content in spinach to which glutathione has been supplied under a high temperature condition assuming that such a quantity under a control condition is 1.

FIG. 8 and FIG. 9 show amino acid contents of spinach subjected to a glutathione treatment, assuming that amino acid contents under a control condition are 1. As shown in FIG. 8, an effect by glutathione under the low temperature condition was observed in part of amino acids, and the effect was small. Meanwhile, as shown in FIG. 9, various amino acid contents were increased under the high temperature condition. This indicates that, in a case of spinach, by supplying oxidized glutathione, amino acid contents of tyrosine, glycine, homoserine, and phenylalanine were increased by 5 or more times. Further, in a case of spinach, it was found that oxidized glutathione was more preferably used than reduced glutathione.

[1: Effect on Free Amino Acid Content by Cultivation Temperature Control of Japanese Mustard Spinach]

A cultivation condition of Japanese mustard spinach, which was a vegetable of the mustard family (Brassicaceae), supplied with glutathione was examined. After Japanese mustard spinach was seeded, and sprouts germinated similarly were selected, were cultivated in an incubator (light period: 14 hours/dark period: 10 hours, light intensity: about 250 μE/m$^2$/s), and were sampled after 28 days. As a cultivation temperature, two types of a low temperature condition LT (Low Temperature: light period 20° C./dark period 15° C.) and a high temperature condition HT (High Temperature: light period 25° C./dark period 20° C.) were set. Note that an appropriate growth temperature range of Japanese mustard spinach was a high temperature condition in this test, however, it is possible to grow Japanese mustard spinach under the low temperature condition without any problem.

As a medium, a soil formed by placing vermiculite (Asahi industrial corporation) as a lower layer, KUREHA seedling raising soil (KUREHA CORPORATION) as a middle layer, and vermiculite (Asahi industrial corporation) as an upper layer at a ratio of 2:1:1 in lamination was used.

In this experiment, only water (Cont.), a 1 mM oxidized glutathione (GSSG) solution, and a 2 mM reduced glutathione (GSH) solution were provided to plants. Specifically, a single individual was put into each pot having about 65 mM (W)×65 mM (D)×50 mM (H), and 25 mL of each solution was provided to roots of each pot once a week.

In the same way as Example 1, a leaf (or a terrestrial part) was measured as a sample in a cation mode and an anion mode of CE-TOFMS (capillary electrophoresis-time-of-flight mass spectrometry: Agilent CE-TOFMS system (Agilent technologies)). By comparing a detected peak with database on the basis of m/Z and a migration period, an amino acid was searched, identified, and quantified. Results thus obtained are shown in FIG. 10 and FIG. 11.

Figure 10:
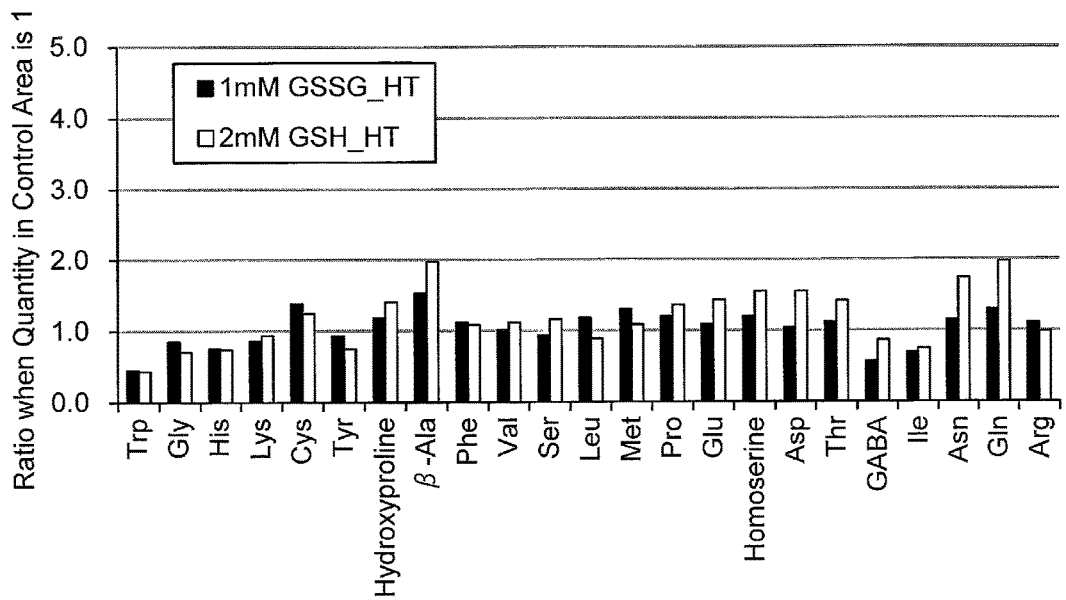
FIG. 10 is a view showing each free amino acid content in Japanese mustard spinach to which glutathione has been supplied under a high temperature condition assuming that such a quantity under a control condition is 1.
Figure 11:
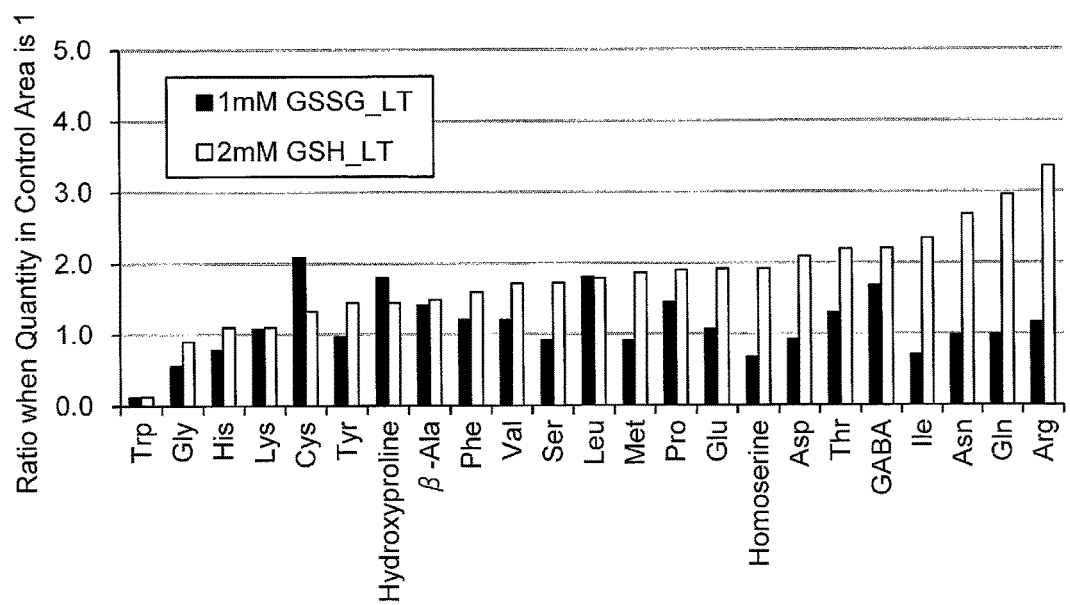
FIG. 11 is a view showing each free amino acid content in Japanese mustard spinach to which glutathione has been supplied under a low temperature condition assuming that such a quantity under a control condition is 1.

FIG. 10 and FIG. 11 show amino acid contents of Japanese mustard spinach subjected to a glutathione treatment, assuming that amino acid contents under a control condition are 1. As shown in FIG. 10, an effect of increase in amino acid content by glutathione under the high temperature condition was observed in part of amino acids such as β-alanine, asparagine, and glutamine. Meanwhile, as shown in FIG. 11, more amino acid contents were increased under the low temperature condition. This indicates that, in a case of Japanese mustard spinach, by supplying reduced glutathione, amino acid contents of aspartic acid, threonine, GABA, isoleucine, asparagine, glutamine, and arginine were increased by 2 or more times. Further, in a case of Japanese mustard spinach, it was found that reduced glutathione was more preferably used than oxidized glutathione.

From the above results, it was clearly found that, by controlling a cultivation temperature, the amino acid content increasing effect by glutathione become more effectively.

Example 4

Examination of Use Concentration of Glutathione for Increasing Amino Acid Content An effect on amino acid contents of garland chrysanthemum which was vegetable of the composite family (Compositae), to which garland chrysanthemum glutathione having various concentrations was supplied, was examined. After garland chrysanthemum was seeded, sprouts germinated similarly were selected, were cultivated in an incubator (light period: 14 hours, 20° C./dark period: 10 hours, 15° C., light intensity: about 250 µE/m²/s), and were sampled after 28 days. As a medium, a soil formed by placing vermiculite (Asahi industrial corporation) as a lower layer, KUREHA seedling raising soil (KUREHA CORPORATION) as a middle layer, and vermiculite (Asahi industrial corporation) as an upper layer at a ratio of 2:1:1 in lamination was used.

In this experiment, only water (Cont.), 0.1 mM, 0.2 mM, 0.5 mM, 1 mM, 2 mM, and 5 mM of oxidized glutathione (GSSG) solutions were provided to plants. Specifically, a single individual was put into each pot having about 65 mM (W)×65 mM (D)×50 mM (H), and 25 mL of each solution was provided to roots of each pot once a week.

In the same way as Example 1, a leaf (or a terrestrial part) was measured as a sample in a cation mode and an anion mode of CE-TOFMS (capillary electrophoresis-time-of-flight mass spectrometry: Agilent CE-TOFMS system (Agilent technologies)). By comparing a detected peak with database on the basis of m/Z and a migration period, an amino acid was searched, identified, and quantified. Results thus obtained are shown in FIG. 12a and FIG. 12b.

As shown in FIG. 12a, by supplying GSSG to garland chrysanthemum, almost all the total free amino acid contents other than undetectable cysteine were changed. In a case where GSSG was 0.1 mM, amino acid contents other than lysine, tryptophane, glycine, and glutamine were decreased, and a total free amino acid content was decreased. In a case where GSSG was used under the condition of 0.2 mM to 5 mM, free amino acid contents under treatment were increased concentration-dependently, as compared with a total free amino acid content under a control condition. This indicates that the contents of the amino acids which have a low effect when GSSG having the low concentration is used are also increased by using GSSG having a high concentration.

FIG. 12b shows a ratio of free amino acid contents under the treatment having respective concentrations, assuming that free amino acid contents under the control condition are 1. As shown in FIG. 12b, in a case where 5 mM of GSSG was used, the total free amino acid content was 24.8 times, which was a specially remarkable effect. Further, in a case where 5 mM of GSSG was used, the contents of glycine, asparagine, histidine, homoserine, glutamine, and arginine became about 100 or more times, and the content in arginine was the most remarkable increase, which was 1070 times.

Those results indicate that, in a case where glutathione is used for the purpose of increase in amino acid contents, it was preferable to use an amino acid content promoting agent within the range of 0.2 mM to 5 mM.

Example 5

Examination of Amino Acid Content Increase Effect in Fruit

An effect of glutathione with respect to cherry tomato (breed: Chandelier) which was a vegetable of Solanaceae (nightshade family) was examined. A commercially available seedling was purchased, and was used for an experiment. After the seedling was purchased, the seedling was transplanted to a 1/2000a (are)-sized pot, and was subjected to a conditional cultivation for 6 weeks. As a cultivation soil, 6 L of vermiculite (Asahi industrial corporation) as a lower layer, 3 L of KUREHA seedling raising soil (KUREHA CORPORATION) as a middle layer, and 3 L of vermiculite (Asahi industrial corporation) as an upper layer were used.

After such conditional cultivation, all tomato fruits borne at that time were removed. Then, 20 g of a granule carrier containing 1% of oxidized glutathione or 20 g of a carrier containing 1% of reduced glutathione, processed in the form of granules, (hereinafter, referred to as "GSSG granules" or "GSH granules") was scattered over a ground surface of each pot. This day was determined as Day 0 of this experiment. Further, a control condition having no granules was prepared. An additional manuring was carried out after 8 days, 20 days, 36 days, and 50 days from start of the experiment. As the additional manuring, 6 kg/a (3 g (N 480 mg) per individual) of Kumiai 5604 (N 16%) was used each time. After 20 days, 29 days, and 57 days from the start of the experiment, tomato fruits ripened and turned red were collected, and were used as samples.

In the same way as Example 1, the fruits thus collected were used as samples, and were measured in a cation mode and an anion mode of CE-TOFMS (capillary electrophoresis-time-of-flight mass spectrometry: Agilent CE-TOFMS system (Agilent technologies)). By comparing a detected peak with database on the basis of m/Z and a migration period, an amino acid was searched, identified, and quantified. Results thus obtained are shown in FIG. 13.

FIG. 13 shows ratios of amino acid contents of fruits grown with the GSSG granules or the GSH granules to amino acid contents of a fruit under the control condition. In a case where the GSSG granules were used, the amino acid contents of a fruit collected after 20 days from a granule treatment were increased. Further, in a fruit collected after 29 days from the granule treatment, all the amino acid contents were increased, and a total free amino acid content was increased to 2.2 times. Meanwhile, also in a case where the GSH granules were used, some amino acid contents were increased after 20 days from the granule treatment, and all the amino acid contents were increased in a fruit after 29 days therefrom. A total free amino acid contents of a plant treated with the GSH granules was 1.5 times as much as that of the control condition, so that it was found that the GSSG granules were more preferably used.

In a fruit collected after 57 days from the granule treatment, amino acid contents became closer to those of the control condition. This indicates that an effect of granule supplied at Day 0 was weakened.

An effect of a nitrogen fertilizer manured additionally after 20 days from the granule treatment was examined, and the total free amino acid content under the control condition is decreased, whereas amino acid contents with use of GSSG granules were increased.

Those results indicate that the method of the present invention can increase amino acid contents of not only leaves but also fruits of a plant. Further, glutathione for use in the present invention is not limited in a specific dosage form, and can be used in the form of not only liquid but also, for example, granules for retaining glutathione.

Example 6

Examination of Amino Acid Content Increase Effect of Chinese Chive

An amino acid content increase effect of Chinese chive which was monocotyledon (amaryllis family) was examined. Seeds of a Chinese chive plant were seeded on Jun. 8, 2011 under the condition of 3 seeds/hole in a cell tray (128 holes), and were grown. After that, the Chinese chive plants were transplanted to pots (1/5000 a (are)) on Sep. 12, 2011 under the condition of 6 plants/pot. As a soil, 3 L/pot of a mixture of decomposed granite soil:pearlite:peat moss at a ratio of 2:1:1 was used. As a base fertilizer, 4 g/pot of Kokei (Solid) No. 30 (N-P-K:10-10-10) was used. Hydroponic soil culture was carried out on the pot, and Ootsuka Youeki Dokou (Ootsuka hydroponic soil culture) No. 5 (N-P-K:12-20-20) diluted to EC 0.6 to 1.0 dS/m was additionally manured twice to three times a day at the same time as supply of water.

As glutathione, 4.8 g/pot of GSSG granules was supplied on Jul. 31, 2012. An edible part collected after 4 weeks from supply of the granules was used to measure amino acid contents. the edible part was used as a sample, and was measured in a cation mode and an anion mode of CE-TOFMS (capillary electrophoresis-time-of-flight mass spectrometry: Agilent CE-TOFMS system (Agilent technologies)) in the same way as Example 1. By comparing a detected peak with database on the basis of m/Z and migration time, an amino acid was searched, identified, and quantified. Results thus obtained are shown in FIG. 14.

Figure 14:
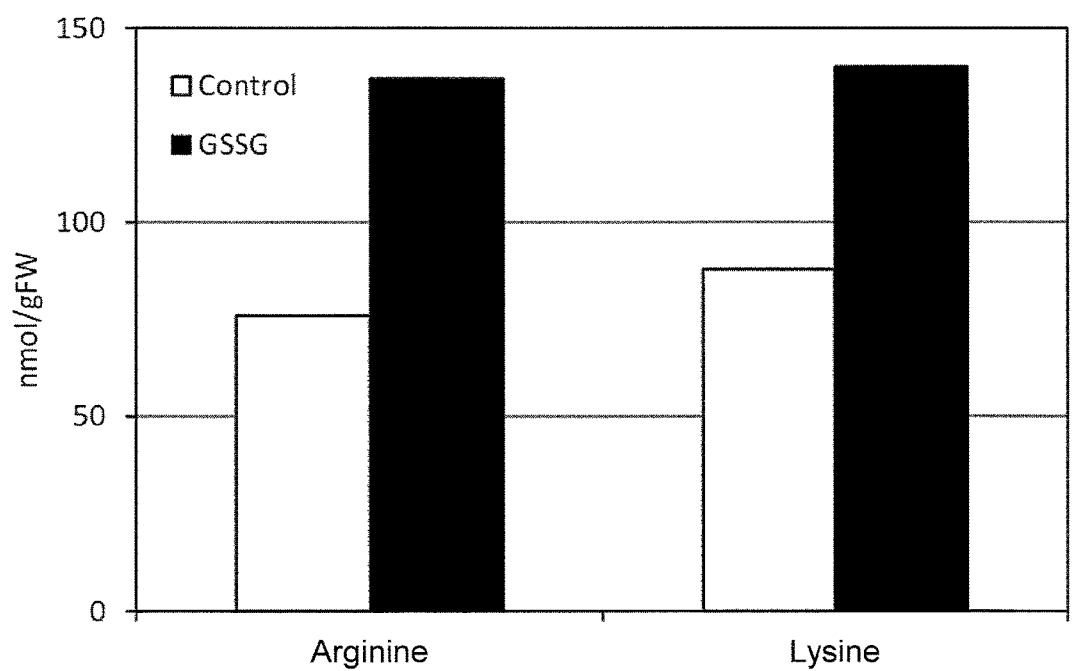
FIG. 14 is a view showing an arginine content and a lysine content in Chinese chive to which granular glutathione has been supplied.

FIG. 14 shows an arginine content and a lysine content in Chinese chive subjected to a GSSG treatment. In comparison with a GSSG untreated condition (control), the arginine content under the GSSG granule treatment (GSSG) was increased to 1.8 times, and the lysine content therein was increased to 1.6 times. From this, it was found that the amino acid content in the Chinese chive which was a monocotyledon was also increased by a glutathione treatment.

As Described Above, the Present Invention can be the Following Forms:

[1] A composition for increasing an amino acid content in a plant, comprising an amino acid content promoting agent.
[2] A composition of 1, wherein the amino acid content promoting agent is glutathione or derivatives thereof.
[3] The composition of 1 or 2, wherein the amino acid content promoting agent is oxidized glutathione, reduced glutathione, or esters thereof.
[4] The composition of 1 to 3, wherein the composition is in the form of liquid, tablets, powders, or granules.
[5] The composition of 1 to 4, wherein the composition does not contain a nitrogen source.
[6] The composition of 1 to 5, for use in producing a plant having an increased amino acid content.
[7] A kit for increasing an amino acid content in a plant, comprising an amino acid content promoting agent or a composition containing the amino acid content promoting agent.
[8] The kit of 7, further comprising instructions in which procedures for increasing an amino acid content in a plant is described.
[9] The kit of 7 or 8, for use in producing a plant having an increased amino acid content.
[10] A method of increasing an amino acid content in a plant, comprising the step of supplying an amino acid content promoting agent or a composition containing the amino acid content promoting agent to a plant.
[11] The method of 10, further comprising the step of cultivating a plant in the presence of the amino acid content promoting agent.
[12] The method of 11, wherein the amino acid content promoting agent having a concentration range of 0.1 mM to 5 mM is brought into contact with a plant.
[13] The method of 11 or 12, wherein a total amount of the amino acid content promoting agent supplied per individual plant falls within the range of 12.5 mg to 300 mg.
[14] The method of 11 to 13, wherein the total amount of the amino acid content promoting agent supplied per litter of soil falls within the range of 60 mg to 1450 mg.
[15] The method of 10 to 14, further comprising the step of measuring the amino acid content in the plant to which the amino acid content promoting agent has been supplied.
[16] The method of 10 to 15, further comprising the step of measuring an amino acid content in a crop of interest of the plant supplied with the amino acid content promoting agent.
[17] The method of 10 to 16, wherein said supply is successively or intermittently carried out.

[18] The method of 10 to 17, further comprising the step of controlling a light condition of a harvesting stage of the plant.

[19] The method of 10 to 18, further comprising the step of controlling a temperature condition of a cultivate time of the plant.

[20] A method of producing a plant having an increased amino acid content, wherein the steps of 10 to 19 are employed.

[21] The method of 20, further comprising the steps of selecting a plant whose amino acid content is increased more than a plant which is cultivated in the absence of the amino acid content promoting agent.

[22] The method of 20 or 21, further comprising the step of selecting, from a crop of interest, a plant whose amino acid content is increased more than a plant which is cultivated in the absence of the amino acid content promoting agent.

[23] The method of 20 to 22, further comprising the step of selecting a plant having a metabolite production amount profile or a gene expression profile which is characteristic in the plant cultivated in the presence of the amino acid content promoting agent.

[24] The method of 23, further comprising the step of obtaining the metabolite production amount profile or the gene expression profile in the plant.

[25] The method of 1 to 24, wherein a subject plant is a land plant.

[26] The method of 1 to 24, wherein a subject plant is an aquatic plant.

[27] The method of 26, wherein the aquatic plant is algae.

[28] A plant produced by the method of 20 to 27.

[29] The plant of 28, being a land plant.

[30] The plant of 28, being an aquatic plant.

[31] The plant of 30, wherein the aquatic plant is algae.

Note that an amino acid whose content is increased in a plant by the amino acid content promoting agent for use in 1 to 31 above differs depending on species of plant, and is not particularly limited, however, is preferably at least one amino acid selected from the group consisting of GABA, a glutamic acid, β alanine, an aspartic acid, alanine, lysine, threonine, hydroxyproline, leucine, serine, tryptophane, valine, tyrosine, phenylalanine, proline, isoleucine, glycine, asparagine, histidine, homoserine, glutamine, and arginine, and is more preferably at least one amino acid selected from the group consisting of proline, isoleucine, glycine, asparagine, histidine, homoserine, glutamine, and arginine, and is particularly preferably arginine.

The present invention is not limited to the description of the embodiments above, and can be modified in numerous ways by a skilled person as long as such modification falls within the scope of the claims. An embodiment derived from a proper combination of technical means disclosed in different embodiments is also encompassed in the technical scope of the present invention.

INDUSTRIAL APPLICABILITY

According to a composition of the present invention, it is possible to easily produce a plant having an increased amino acid content, so that the present invention is applicable to industries such as agricultural, food, etc. industries. The present invention can be applied to all plants and agricultural products, which is an extremely wide range. In consideration of recent health consciousness, marketability of a plant having an increased amino acid content is high.

The invention claimed is:

1. A method of producing a plant having an increased amino acid concentration, the method comprising:
   supplying to a plant, a solution containing oxidized glutathione at a concentration of 2 mM to 5 mM or reduced glutathione at a concentration of 5 mM; and
   measuring the amino acid content in the plant supplied with the solution.

2. The method as set forth in claim 1, further comprising selecting a plant whose amino acid concentration is increased more than a plant which is cultivated in the solution.

3. The method as set forth in claim 1 or 2, further comprising selecting a plant having a metabolite production amount profile or gene expression profile which is characteristic in the plant cultivated in the presence of the solution.

4. A plant produced by the method as recited in claim 1.

5. A method of increasing an amino acid concentration in a plant, the method comprising:
   supplying to a plant, a solution containing oxidized glutathione at a concentration of 2 mM or to 5 mM reduced glutathione at a concentration of 5 mM; and
   measuring the amino acid content in the plant supplied with the solution.

6. The method as set forth in claim 5, further comprising at least one of:
   cultivating the plant in the presence of the solution;
   controlling a light condition in a harvesting stage of the plant;
   controlling a temperature condition during a cultivation period of the plant; or
   a combination thereof.

7. The method as set forth in claim 6, wherein the plant is harvested during a period after 8 or more hours pass from start of controlling the light condition but before completion of controlling the light condition.

8. The method as set forth in claim 6, wherein controlling the temperature condition is carried out after supplying, to the plant, the solution.

9. The method of claim 5, wherein an amount of the oxidized glutathione or reduced glutathione supplied per liter of soil falls within a range of 580 mg to about 1450 mg.

* * * * *